(12) United States Patent
Gladyshev et al.

(10) Patent No.: US 6,849,417 B1
(45) Date of Patent: Feb. 1, 2005

(54) MAMMALIAN SELENOPROTEIN DIFFERENTIALLY EXPRESSED IN TUMOR CELLS

(75) Inventors: Vadim N. Gladyshev, Lincoln, NE (US); Dolph L. Hatfield, Washington, DC (US); Kuan-Teh Jeang, Rockville, MD (US); Alan Diamond, Naperville, IL (US); John C. Wootton, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 293 days.

(21) Appl. No.: 09/676,718

(22) Filed: Sep. 28, 2000

Related U.S. Application Data

(63) Continuation of application No. PCT/US99/07560, filed on Apr. 6, 1999.
(60) Provisional application No. 60/080,850, filed on Apr. 6, 1998.

(51) Int. Cl.$^7$ ........................ G01N 33/574; C07K 16/00
(52) U.S. Cl. .................... 435/7.23; 435/6; 436/501; 530/387.7; 530/387.3; 530/389.7
(58) Field of Search ........................... 435/7.23, 6, 7.1, 435/4; 530/387.7, 387.3, 389.7; 436/501, 64

(56) References Cited

U.S. PATENT DOCUMENTS 5,356,817 A * 10/1994 Cole ........................... 436/64

FOREIGN PATENT DOCUMENTS

WO    WO 98-42738    10/1998

OTHER PUBLICATIONS

De Plaen E, et al. Immunogenetics 1994; 40: 360–9.*
Gladyshev VN, et al. Biochem Biophys Res Commun Oct. 20, 1998; 251 (2): 488–93.*
Mork H, et al. Nutr Cancer 2000; 37 (1): 108–16.*
Kumaraswamy E, et al. J Biol Chem Nov. 10, 2000; 275 (45): 35540–7.*
Kote–Jarai Z, et al. Prostate Cancer Prostatic Dis 2002; 5 (3): 189–92.*
Early DS, et al. Am J Gastroenterol May 2002; 97 (3): 745–8.*
Calvo A, et al. Cancer Res Sep. 15, 2002; 62 (18): 5325–35.*
Li X, et al. Growth Factors 2001; 19 (1): 49–59.*
Ward AM. Development Oncology 1985; 21: 90–106.*
Gail MH. Immunol Ser. 1990; 53: 13–25.*
Tockman MS, et al. Cancer Res. May 1, 1992; 52 (Suppl.):2711s–2718s.*
Rae FK, et al. Int J Cancer 2000; 88: 726–32.*
Skolnick J, et al. Trends Biotechnol Jan.; 2000; 18 (1): 34–9.*
Gladyshev et al., "Selenium in Normal and HIV–Infected Human T Cells: Discovery of a Novel Selenoprotein" *FASEB J.* 11(3): A235, 1997.
Proia, "Gene encoding the human β chain: Extensive homology of intron placement in the α– and β–chain genes" *Proc. Natl. Acad. Sci. USA* 85: 1883–1887, 1988.
Gamble et al., "Selenium–dependent Gluththione Peroxidase and other Selenoproteins: Their Synthesis and Biochemical Roles" *J. Chem. Tech. Biotechnol.*, 68: 123–134, 1997.
Gladyshev et al., "A New Human Selenium–containing Protein: Purification, Characterization, and cDNA Sequence" *J. Biol. Chem.* 273(15):8910–8915, 1998.
Clark et a., "Effects of Selenium Supplementation for Cancer Prevention in Patients with Carcinoma of the Skin: A Randomized Controlled Trial" *JAMA*, 276(24), 1957–1963, 1996.

* cited by examiner

*Primary Examiner*—Christina Chan
*Assistant Examiner*—Stephen L. Rawlings
(74) *Attorney, Agent, or Firm*—Klarquist, Sparkman, LLP

(57) ABSTRACT

A 15 kDa selenium-containing protein ("selenoprotein") is disclosed. The protein is shown to be differentially expressed in cancer cells, such as prostate cancer cells. There is a correlation between the presence of a polymorphism at nucleotide positions 811 and 1125 of the 15 kDa selenoprotein gene, and the presence of cancer. This polymorphism is more prevalent in the African American population. The determination of an individual's genotype may be used as an indicator of the need for dietary selenium supplementation to inhibit tumor development. Compositions including the isolated protein, specific binding agents that recognize the protein, as well as underlying nucleic acid sequences are presented, as are methods of using such compositions.

13 Claims, 8 Drawing Sheets

FIG. 1

```
AGCGATGGCGGCTGGGCCGAGTGGGGTGTCTGGTGCTGGCCGGTGTTGGGCTACGGTGTTGTTGGGCACTGTGCTTCAAGCGGTGTCTGCTTTGGGGCAGAGTTTCATCGGAGGCATGCAG  120
 m  a  a  g  p  s  g  c  l  v  p  a  f  g  l  r  l  l  l  a  t  v  l  g  a  v  S  A  R  F  G  A  E  F  S  S  E  A  C  R

AGAGTTAGGCTTTTCTAGCAACTGCTTGCTCTGTGCAGCTCTTTGAGCTGAGATCCTGAGCTGATTGCAGAGGATGCTGTCAGGAGGAAGCACAATTTGAAAC  240
 E  L  G  F  S  S  N  L  L  C  S  S  C  D  L  L  G  Q  F  N  L  Q  L  D  P  D  C  R  G  C  C  Q  E  E  A  Q  F  E  T

CAAAAAGCTGTATGCAGGAGCTATTCTTGAAGTTGTGGAATGAAAATTGGGAAGGTTCCCTCAAGCTTTTGTTAGGAGTGATGATAAAACCAAAGCCCAAACTGTTCAGAGACTGCAAATCAA  360
 K  K  L  Y  A  G  A  I  L  E  V  C  G  U  K  L  G  R  F  P  P  Q  V  Q  A  F  V  R  S  D  K  P  K  L  F  R  G  L  Q  I  K

GTATGTCCGTGGTTCAGACCCTGTATTAAAGCTTTTGGACGACGACAATGGGAACATTGCTGAAGAATGTGAAGAAGAACATTCTCAAATGGAACAGAGTCCTGAGTGAAAAGTT  480
 Y  V  R  G  S  D  P  V  L  K  L  L  D  D  D  N  G  N  I  A  E  E  L  S  I  L  K  W  N  T  D  S  V  E  E  F  L  S  E  K  L

GGAACCGCATATAAATCTGCTAAATTTGTCCTATCCTTTGTACCTTTACCTTATCAAATGAAATATTACAGACACCTAGAAAATAATTAGTTTGCTTGCCTTGATCAGTCTTTTACT  600
 E  R  I  *

TGAGGCATTAAATATCTAATTAAATCGTCAGATAGTCCATCATATCTAAGGAGTTGGCAAGCTTAACAAAACCATTTTATAAATGTCCATCCTCCTGCATTGTTGATA  720
CCACTAACAAATGCTTTGTACAGACTTGTGCGGTTAATTATGCAAATACGAGCTAAGTCCCAGTTTGTGATAATTGGTCAAATAGATATTTCTAAATTAGAGAGGTTAACAAGACAGATGA  840
TTACTATGCCTCATGTGCTGTGTGTCTCTTTGAAGGAATGACAGCAGTACTGAGCCTGCTGCCCTGCAGAGATTGCCCTGCTCTCCTATTTTGTATT  960
ACCCAGCTTTCTTTTTAATGTATTTATTTATAGTTTACAATGGACACTGCTAATGAATGAACTTTGTAAACATATTCAAGATCCTACAGTAAGAGTGAAACATT  1080
CACAAAGATTTGCGTTAATGAAGACTACACAGAAACCTTTCTAGGGATTGTGTGTGAGTCAGATACATACTTGGCAAATTTTGAGTTTACATTCTTACAGAAAAGTCCATTAAAAGT  1200
GATCATTTGTAAGACCAAAATATAAATAAAAGTTTCAAAAATC  1244
```

FIG. 2

```
Rice (partial)      GRRLVLTS--CSVLCLGAEGFG-ARECEELGFTGLAL-CSDCN
                    * **   *   * * *     * ****    *  **  *

15K HUMAN   MAAGPSGCLVPAFGLRLLLATVLQAVSAFGAEFSS--EACRELGFSSNLL-CSSCDLLGQFNLLQLDPDCRGCCQEEAQFETK    1-80
15K MOUSE   MAAGQGGWLRPAJGLRLLLATAFQAVSALGAEFAS--EACRELGFSSNLL-CSSCDLLGQFNLLPLDPVCRGCCQEEAQFETK    1-80
            ****   **   ** **** ** **** ****    ******** *** **********     ** ** **********
C. elegans  GWIFLLLAAVVSPMFGEVEEYKIDVEECKAAGFNPETLKCGLCERLSDYHLETLLTDCLQCCIKEEEFKHE
                                * *    *     * **        *  * *  ** * * * *
Brugia malayi (partial)   KDYAEMEQE
                           *      *

15K HUMAN   KLYAGAILEVCG U KLGRFPQVQAFVRSDKPKLFRG-LQIKYVRGSDPVLKLLDDNGNIAEELSILKWNTDSVEEFLSEKLERI   81-162
15K MOUSE   KLYAGAILEVCG U KLGRFPQVQAFVRSDKPKLFRG-LQIKYVRGSDPVLKLLDDNGNIAEELSILKWNTDSVEEFLSEKLERI   81-162
            ** ********   ***************** **** ******************************************
C. elegans  K-YPTAILEVCE C NLARFPQVQAFVHKDMARQFGGKVKVKHVRGVRPQVALKDADFKXKEVLSVEKWDTDTLIDFFNQWLE
            *  * ***** *   * ************  *  * *  *   * *   * *  *   *  *******   *   **
B. malayi   K-YPRAHIEICE C NLGRFPQAEAFVKSNMVKKWGTCVKVHHVRGTLPTIKLLDAQGEVQKTMNIEKWDTDTITEFLNTWLE
            *  *    *  *   ** **** * *  * *    *    **   *   **   **   *  ***         * **
```

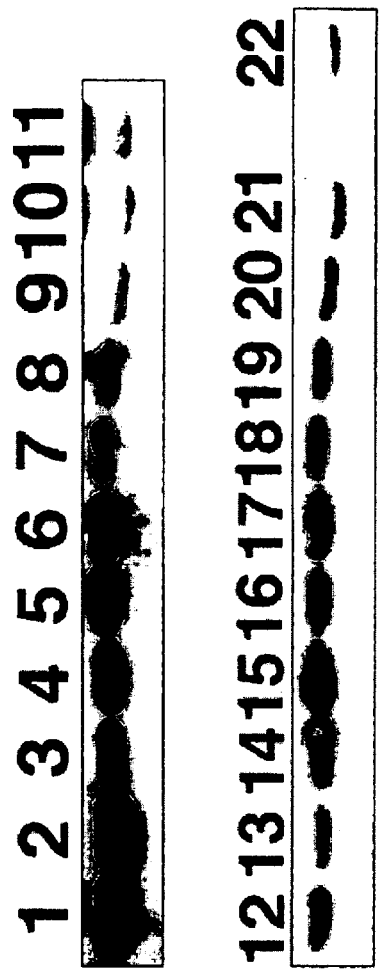
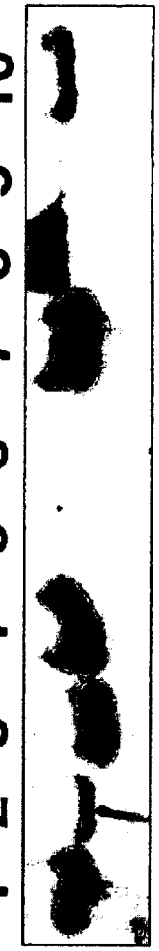
FIG. 4
FIG. 5
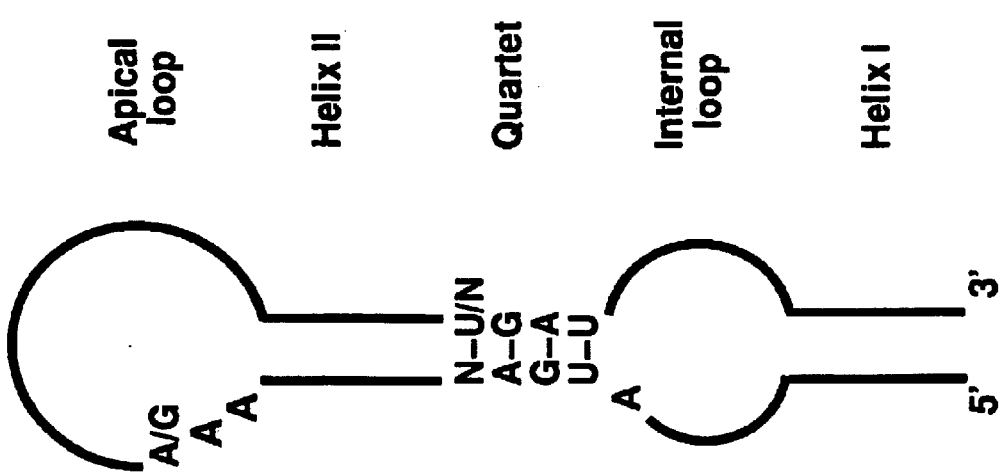
FIG. 3A

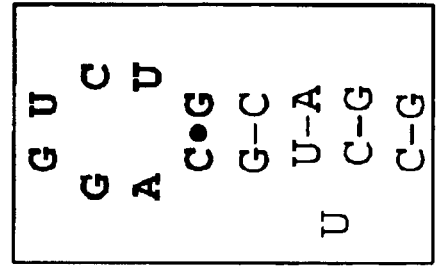
FIG. 9A
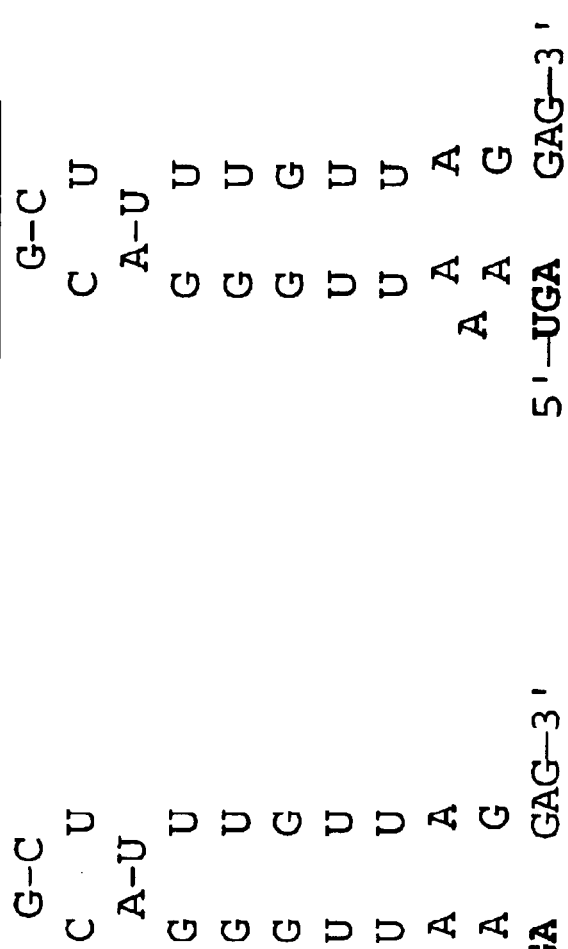
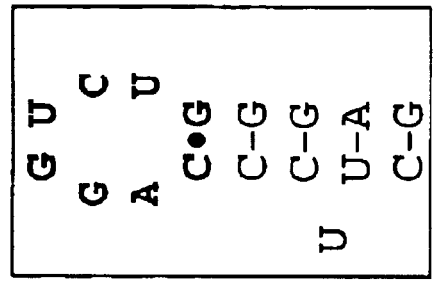
FIG. 9B
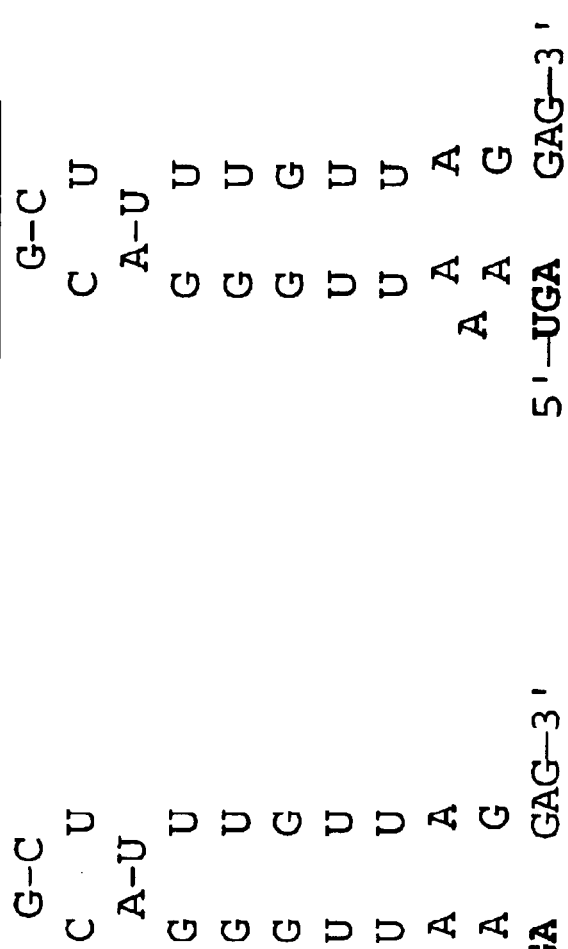
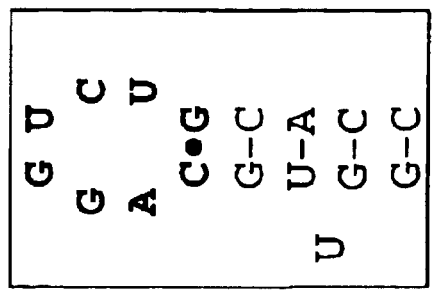
FIG. 9C
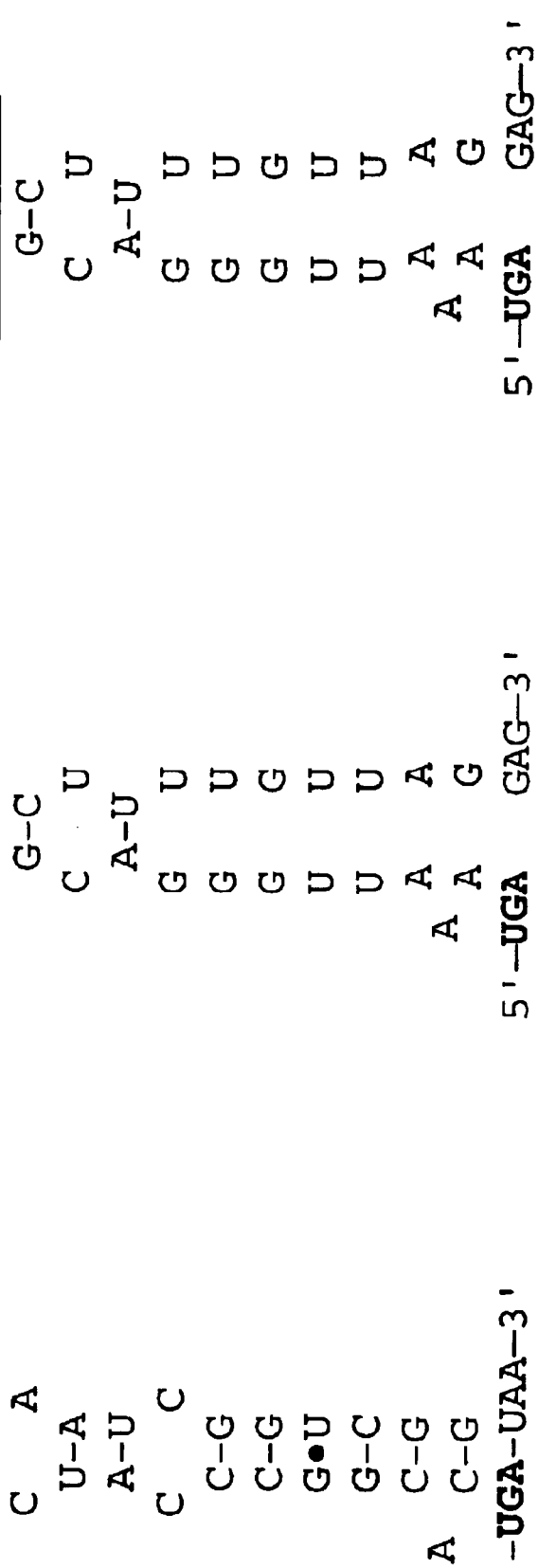

US 6,849,417 B1

MAMMALIAN SELENOPROTEIN DIFFERENTIALLY EXPRESSED IN TUMOR CELLS

CROSS REFERENCE TO RELATED APPLICATIONS

This is a continuation of PCT/US99/07560 filed Apr. 6, 1999, which claims the benefit of U.S. Provisional Application No. 60/080,850, filed Apr. 6, 1998, both of which are incorporated by reference.

FIELD OF THE INVENTION

This invention relates to a mammalian selenocysteine-containing protein that is shown to be differentially expressed in tumor and non-tumor cells. Methods of using the protein, antibodies that bind to the protein and corresponding nucleic acid molecules are disclosed. In addition, methods of using the nucleic acid molecules to determine the genotype of an individual, is disclosed.

BACKGROUND OF THE INVENTION

Selenium has been implicated in immunological function and many other biological processes through various nutritional and biochemical studies (Lee et al., 1997, *Molecules & Cells* 6:509–20; Hatfield et al., 1999, *Comprehensive Natural Products Chemistry*, 4, 353–80; Gladyshev and Hatfield, 1999, *J. Biomed. Sci.*, in press). Recent studies have shown that supplementation of the diet with selenium resulted in 63% reduction in human prostate cancer and, to a lesser extent, in the reduction of colon and lung cancers (Clark et al., 1996, *JAMA*, 276:1957–63).

Selenium, a trace element, is a natural component of several prokaryotic and eukaryotic proteins. Although selenium occurs in prokaryotic proteins either as a cofactor or as a selenocysteine residue, mammalian selenoproteins identified thus far contain selenium only in the form of selenocysteine, which is the 21st naturally occurring amino acid in protein. A selenocysteine tRNA that decodes UGA has been found in all life kingdoms, suggesting that the use of UGA as a codon for selenocysteine is widespread in nature (Hatfield and Diamond, 1993, *Trends Genet.* 9:69–70). The special conserved stem-loop structures in the 3'-untranslated regions of mammalian selenoprotein mRNAs are essential for recognition of UGA as a codon for selenocysteine, rather than a codon for termination of translation (Low and Berry, 1996, *Trends Biochem. Sci.* 21:203).

Of the eleven genes encoding different selenocysteine-containing proteins that have been found thus far in mammals, four encode various glutathione peroxidases (reviewed in Sunde, 1994, In: *Selenium in Biology in Human Health*, ed. Burk, R. F. (Springer, N.Y.), pp. 146–77; and Ursini et al., 1995, *Methods Enzymol.* 252:38–53), three encode different thyroid hormone deiodinases (Berry et al., 1991, *Nature*, 349:438; Croteau et al., 1996, *J. Clin. Invest.* 98:405; and St. Germain et al., 1994, *Proc. Natl. Acad. Sci. USA.* 91:7767), and others encode thioredoxin reductase (Gasdaska et al., 1995, *FEBS Lett.* 373:5), selenophosphate synthetase 2 (SPS2) (Guimaraes et al., 1996, *Proc. Natl. Acad. Sci. USA* 93:15086–91), selenoprotein P (Hill and Burk, 1994, In: *Selenium in Biology in Human Health*, ed. Burk, R. F. (Springer, N.Y.), pp. 117–32) and selenoprotein W (Vendeland et al., 1995, *Proc. Natl. Acad. Sci. USA* 92:8749).

Selenocysteine is located at the active center and is directly involved, or at least implicated, in the catalytic reactions catalyzed by glutathione peroxidases, thyroid hormone deiodinases and selenophosphate synthetase 2. Thioredoxin reductase contains selenocysteine (Tamura and Stadtman, 1996, *Proc. Natl. Acad. Sci. USA*, 93:1006–11) in a novel C-terminal Gly-Cys-Sec-Gly redox motif (Gladyshev et at., 1996, *Proc. Natl. Acad. Sci. USA* 93:6146–51). This center has been implicated in the peroxidase reaction catalyzed by the enzyme (Gladyshev et al., 1996, *Proc. Natl. Acad. Sci. USA* 93:6146–51) and in a redox interaction with the N-terminal redox disulfide (Arscott et al., 1997, *Proc. Natl. Acad. Sci. USA* 94:3621–6), although further studies are necessary to prove the suggested essential role of selenocysteine in this protein. Selenoprotein P, a protein of unknown function, is unusual in that it contains ten selenocysteine residues. The function of selenoprotein W also remains unknown.

None of the previously characterized selenoproteins is a likely candidate to account for the selenium effect observed in the reported cancer studies. The present invention is directed towards a newly isolated selenoprotein that is differentially expressed in tumor cells.

SUMMARY OF THE INVENTION

The present invention relates to a newly isolated human protein of molecular weight around 15 kDa. The protein contains a single selenocysteine residue, and is herein referred to as the 15 kDa selenoprotein. The mouse homolog of the human 15 kDa selenoprotein is also provided. The 15 kDa selenoprotein is shown to be expressed in a number of mammalian tissues, but is found at particularly high levels in prostate and thyroid tissues. Most notably, the expression of the 15 kDa selenoprotein and its mRNA are altered in several mammalian cancers. For example, the level of the protein was found to be 3–5 fold lower in tumorous hepatic cells in mice than in surrounding non-tumorous hepatic cells. Expression of the protein is also shown to be decreased in prostate cancer cell lines compared to healthy prostate cell lines.

The cDNA sequence of the human 15 kDa selenoprotein is 1244 nucleotides in length and contains an open reading frame encoding a 162 amino acid protein. The 3' untranslated (UTR) region of the cDNA (i.e., the region downstream of the ORF) contains a stem-loop selenocysteine insertion sequence (SECIS) element. Such SECIS elements have been shown to be essential for insertion of selenocysteine into proteins at a UGA codon in coding sequences of other selenocysteine-containing proteins. Two polymorphisms were detected in the 3' UTR of the human 15 kDa selenoprotein cDNA, one of which was located in the SECIS element. A link between this polymorphism pattern and cancer was strongly suggested after the determination and subsequent analysis of the genotype of over 200 individuals. In addition to the link between the polymorphism pattern within the 15 kDa selenoprotein cDNAs and cancer, a link was noted between the polymorphism and race.

One aspect of the invention is a purified preparation of the 15 kDa selenoprotein, as well as immunologically active fragments of this protein and specific binding agents, such as monoclonal antibodies, that specifically bind to the protein. Such specific binding agents may be used to detect and quantify the presence of the 15 kDa selenoprotein in biological samples, and may be used in methods for detecting susceptibility to, or the presence of, cancer or monitoring the progression of the cancerous state.

Also provided by the invention is a nucleic acid molecule encoding the 15 kDa selenoprotein, as well as probes and primers that are useful to detect and quantify the nucleic acid molecule. Probes and primers that are useful to detect polymorphisms in the cDNA sequence and the gene corresponding to the 15 kDa selenoprotein are also disclosed. Probes and primers that are useful to determine the genotype of an individual's 15 kDa selenoprotein are also disclosed. The detection of polymorphisms in the 15 kDa selenoprotein cDNA or gene, and the determination of an individual's genotype, may be used to determine the susceptibility of an individual to cancer, including prostate cancer.

In other embodiments, the invention also provides compositions and methods useful to determine the effect of chemical and biological agents (such as candidate tumor therapeutics) on the expression of the 15 kDa selenoprotein. In one such embodiment, the effect of exposing cells to the candidate agent is assessed by measuring the change in expression levels of the 15 kDa selenoprotein mRNA or protein within the cell after exposure to the agent. Such methods may be used to identify agents that have beneficial effects in the treatment or prevention of cancer, including prostate cancer.

BRIEF DESCRIPTION OF THE DRAWINGS

FIG. 1 shows the human cDNA sequence (SEQ ID NO: 2) encoding the 15 kDa selenoprotein and the amino acid sequence (SEQ ID NO: 1) of the selenoprotein itself. In the deduced amino acid sequence, the putative signal peptide is shown in lower case and the most probable site of post-translational cleavage is indicated by an upward arrow. The amino acid U represents selenocysteine 93 encoded by an in-frame TGA codon (overlined). The sequences of four tryptic peptides, for which amino acid sequences were experimentally determined, are underlined. In the 3'-UTR, the positions of the selenocysteine insertion sequence (SECIS element) and the poly-A addition signal (dotted underline) are shown.

FIG. 2 shows alignment of the human 15 kDa selenoprotein sequence (SEQ ID NO: 1) with homologs from mouse (SEQ ID NO: 9), nematodes (C. elegans SEQ ID NO: 16, B. malayi SEQ ID NO: 17) and rice (SEQ ID NO: 18).

FIGS. 3A and 3B relate to the SECIS element. FIG. 3A shows the general features of eukaryotic SECIS elements used to identify a matching element in the 3'-UTRs of the mRNAs encoding human and mouse 15 kDa selenoproteins. FIG. 3B shows an alignment of the predicted SECIS elements of the human (nucleotides 1083–1164 of SEQ ID NO: 2) and mouse mRNAs (nucleotides 1049–1127 of SEQ ID NO: 8) encoding the 15 kDa selenoprotein with a typical experimentally verified example (human GPX-1, SEQ ID NO: 19). In helical stems, single base bulges or mismatches are shown by gaps in the arrows. A lower case "a" residue above the human apical loop sequence indicates a polymorphism at position 1125.

FIG. 4 is a digital image of a Western blot showing the detection of the 15 kDa selenoprotein in cancerous and non-cancerous mouse liver tissues.

FIG. 5 is a digital image of a Western blot showing the detection of the 15 kDa selenoprotein in mouse cancerous and non-cancerous liver and prostate tissues.

FIG. 9 shows the bacterial selenocysteine insertion sequence elements. These structures show the formate dehydrogenase H selenocysteine insertion sequence element (A) and two selenocysteine insertion sequence elements (B and C) designed downstream of the TGA codon encoding selenocysteine in the 15 kDa selenoprotein gene. The minimal essential structure necessary for selenocysteine incorporation is boxed. 5'-end UGA encodes selenocysteine in these three constructs.

SEQUENCE LISTING

Figure 3B:
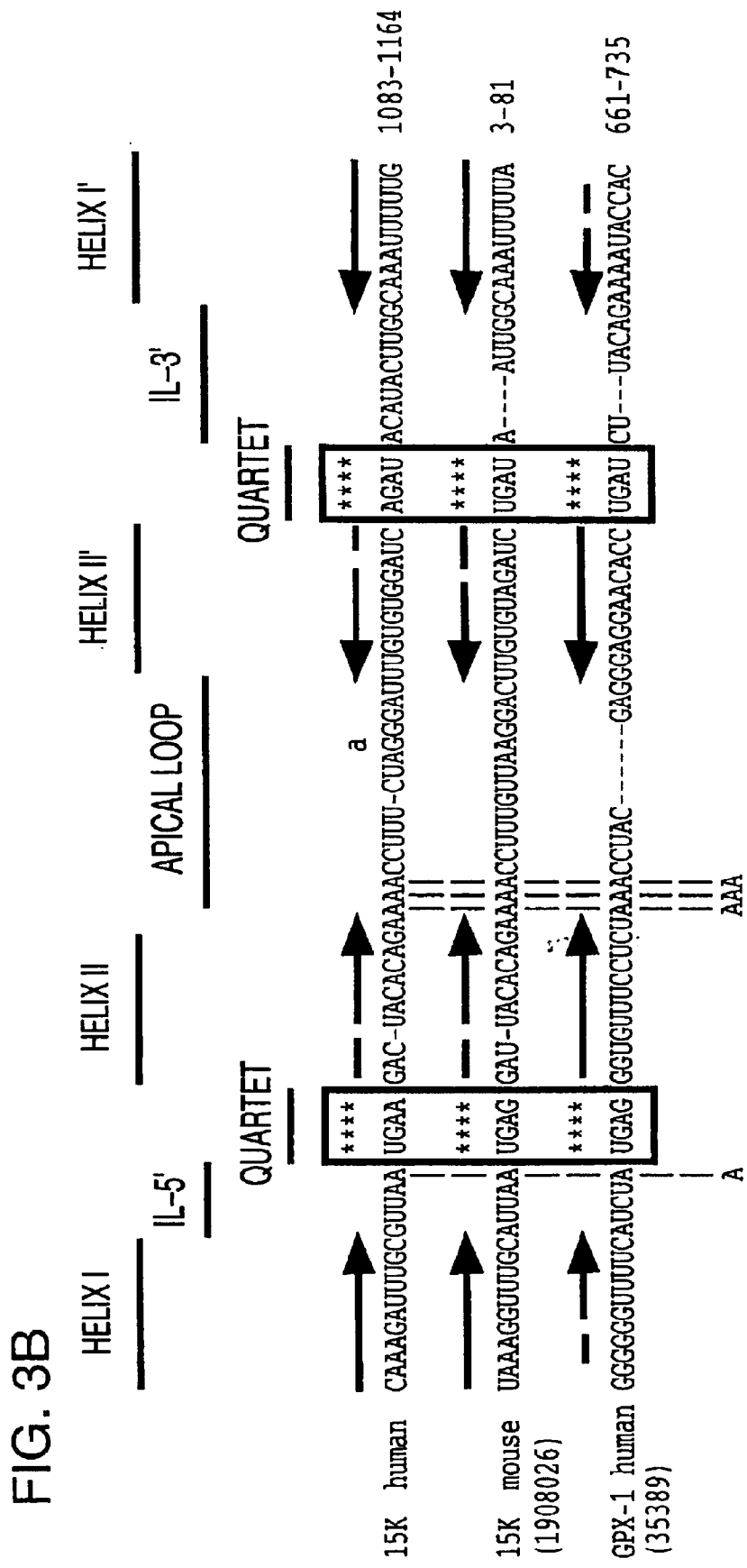

The nucleic and amino acid sequences listed in the accompanying sequence listing are shown using standard letter abbreviations for nucleotide bases, and three letter code for amino acids. In those sequence listings showing amino acid sequences, selenocysteine is represented by Xaa. Only one strand of each nucleic acid sequence is shown, but the complementary strand is understood as included by any reference to the displayed strand.

Seq. I.D. No. 1 shows the amino acid sequence of the human 15 kDa selenoprotein.

Seq. I.D. No. 2 shows the nucleic acid sequence of the human 15kDa selenoprotein cDNA.

Seq. I.D. No. 3 shows the nucleic acid sequence of the ORF of the human 15 kDa selenoprotein cDNA.

Seq. I.D. No. 4 shows the amino acid sequence of the putative mature form of the human 15 kDa selenoprotein after post-translational modification.

Seq. I.D. Nos. 5–7 show examples of primers that may be used to amplify portions of the human 15 kDa selenoprotein cDNA.

Seq. I.D. No. 8 shows the nucleic acid sequence of the mouse 15 kDa selenoprotein cDNA.

Seq. I.D. No. 9 shows the amino acid sequence of the mouse 15 kDa selenoprotein.

Seq. I.D. Nos. 10 and 11 show examples of primers that may be used to amplify portions of the mouse 15 kDa selenoprotein cDNA.

Seq. I.D. Nos. 12 and 13 show examples of primers that may be used to amplify the polymorphism containing region of human 15 kDa selenoprotein cDNA.

Seq. I.D. No. 14 shows a primer that can be used to determine the nucleotide at position 811 using primer extension.

Seq. I.D. No. 15 shows a primer that can be used to determine the nucleotide at position 1125 using primer extension.

SEQ ID NO: 16 shows a C. elegans protein sequence with homology to SEQ ID NO: 1.

SEQ ID NO: 17 shows a Brugla malayi protein sequence with homology to SEQ ID NO: 1.

SEQ ID NO: 18 shows a Oryza sativa (rice) protein sequence with homology to SEQ ID NO: 1.

SEQ ID NO: 19 shows a partial human glutathione peroxidase (GPX-1) nucleic acid sequence with homology to SEQ ID NOS: 2 and 8.

DETAILED DESCRIPTION OF THE INVENTION

I. Abbreviations and Definitions

The following abbreviations and definitions are used herein.

Sec—selenocysteine
IPTG—isopropyl β-D-thiogalactopyranoside
ORF—open reading frame
EST—expressed sequence tag
dbEST—database of expressed sequence tags
MALDI—matrix assisted laser desorption ionization
3'-UTR—3' untranslated region
SECIS element—selenocysteine insertion sequence element
CGAP—Cancer Gene Anatomy Project
GPX—glutathione peroxidase
TFA—trifluoroacetic acid cDNA (complementary DNA): A piece of DNA lacking internal, non-coding segments (introns). cDNA is synthesized in the laboratory by reverse transcription from messenger RNA extracted from cells.

15 kDa selenoprotein: A mammalian protein of approximate molecular weight 15 kDa that contains a selenocysteine residue encoded in the corresponding gene sequence by the codon UGA. Levels of the 15 kDa selenoprotein are reduced in certain types of tumor cells, such as prostate cancer cells. The present invention discloses the sequences of the human and mouse 15 kDa selenoproteins and their corresponding cDNAs. The term "15 kDa selenoprotein" refers generically to mammalian 15 kDa selenoproteins; the specific human or murine forms are herein referred to as the "human 15 kDa selenoprotein" and the "murine" or "mouse 15 kDa selenoprotein." Mammalian 15 kDa selenoprotein polypeptides and cDNAs are orthologs of the disclosed murine and human 15 kDa sequences and are thus structurally related by the possession of similar amino acid and nucleic acid structures. Typically, mammalian 15 kDa selenoprotein polypeptide sequences are characterized by possession of at least 70% amino acid sequence identity to the human 15 kDa selenoprotein amino acid sequence, determined using the BLAST program as described below.

Sequence identity: the relatedness of two nucleic acid sequences, or two amino acid sequences is typically expressed in terms of the identity between the sequences (in the case of amino acid sequences, similarity is an alternative assessment). Sequence identity is frequently measured in terms of percentage identity; the higher the percentage, the more similar are the two sequences. Homologs of the human and mouse 15 kDa selenoproteins will possess a relatively high degree of sequence identity when aligned using standard methods.

Methods of alignment of sequences for comparison are well known in the art. Various programs and alignment algorithms are described in: Smith and Waterman (*Adv. Appl. Math.* 2:482, 1981); Needleman and Wunsch (*J. Mol. Biol.* 48:443, 1970); Pearson and Lipman (*Proc. Natl. Acad. Sci. USA* 85:2444, 1988); Higgins and Sharp (*Gene* 73:237–44, 1988); Higgins and Sharp (CABIOS 5:151–3, 1989); Corpet et al. (*Nuc. Acid. Res.* 16:10881–90, 1988); Huang et al. (*Computer Applications in the Biosciences* 8:155–65, 1992); and Pearson et al. (*Meth. Mol. Biol.* 24:307–31, 1994). Altschul et al. (*Nature Genet.* 6:119–29, 1994) presents a detailed consideration of sequence alignment methods and homology calculations.

The NCBI Basic Local Alignment Search Tool (BLAST) (Altschul et al., 1990, *J. Mol. Biol.* 215:403–10) is available from several sources, including the National Center for Biotechnology Information (NCBI, Bethesda, Md.) and on the Internet, for use in connection with the sequence analysis programs blastp, blastn, blastx, tblastn and tblastx. It can be accessed at http://www.ncbi.nlm.nih.gov/BLAST/. A description of how to determine sequence identity using this program is available at http://www.ncbi.nlm.nih.gov/BLAST/blast_help.html.

Homologs of the disclosed 15 kDa selenoprotein are typically characterized by possession of at least 70% sequence identity counted over the full length alignment with the amino acid sequence of a selected transcription factor using the NCBI Blast 2.0, Basic BLAST search, gapped blastp program set to default parameters (BLOSUM62 matrix; Gap existence cost=11; Per residue gap cost=1; lambda ratio=0.85). Proteins with even greater similarity to the reference sequences will show increasing percentage identities when assessed by this method, such as at least 75%, at least 80%, at least 90% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at http://www.ncbi.nlm.nih.gov/BLAST/blast_FAQs.html. One of skill in the all will appreciate that these sequence identity ranges are provided for guidance only; it is entirely possible that strongly significant homologs could be obtained that fall outside of the ranges provided. The present invention provides not only the peptide homologs as described above, but also nucleic acid molecules that encode such homologs.

Homologs of the disclosed 15 kDa selenoprotein nucleic acids are typically characterized by possession of at least 70% sequence identity counted over the full length alignment with the nucleic acid sequence of a selected transcription factor using the NCBI Blast 2.0, Basic BLAST search, blastn program set to default parameters (BLOSUM62 matrix; Gap existence cost=11; Per residue gap cost=1; lambda ratio=0.85). Homologs with even greater similarity to the reference sequences will show increasing percentage identities when assessed by this method, such as at least 75%, at least 80%, at least 90% or at least 95% sequence identity.

An alternative indication that two nucleic acid molecules are closely related is that the two molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology-Hybridization with Nucleic Acid Probes Part* 1, Chapter 2 "Overview of principles of hybridization and the strategy of nucleic acid probe assays", Elsevier, N.Y., 1993). Nucleic acid molecules that hybridize under stringent conditions to a disclosed transcription factor cDNA sequence will typically hybridize to a probe based on either the entire cDNA or selected portions of the cDNA under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Specific binding agent: An agent that binds substantially only to a defined target. Thus a 15 kDa selenoprotein specific binding agent binds substantially only the 15 kDa selenoprotein. As used herein, the term "15 kDa selenoprotein specific binding agent" includes anti-15 kDa selenoprotein antibodies and other agents that bind substantially only to the 15 kDa selenoprotein.

The term "anti-15 kDa selenoprotein antibodies" encompasses monoclonal and polyclonal antibodies that are specific for the 15 kDa selenoprotein, i.e., which bind substantially only to the 15 kDa selenoprotein when assessed using the methods described below, as well as immunologically effective portions ("fragments") thereof. Preferably, the anti-15 kDa selenoprotein antibodies used in the present invention are monoclonal antibodies (or immunologically effective portions thereof) and may also be humanized monoclonal antibodies (or immunologically effective portions thereof). Immunologically effective portions of monoclonal antibodies include Fab, Fab', F(ab')$_2$ Fabc and Fv portions (for a review, see Better and Horowitz, 1989, *Methods Enzymol.* 178:476–96). Anti-15 kDa selenoprotein antibodies may also be produced using standard procedures described in a number of texts, including "Antibodies, A Laboratory Manual" by Harlow and Lane, Cold Spring Harbor Laboratory (1988).

The determination that a particular agent binds substantially only to the 15 kDa selenoprotein may readily be made by using or adapting routine procedures. One suitable in vitro assay makes use of the Western blotting procedure (described in many standard texts, including "Antibodies, A Laboratory Manual" by Harlow and Lane, Cold Spring Harbor Laboratory, New York, 1988). Western blotting may be used to determine that a given 15 kDa selenoprotein binding agent, such as an anti-15 kDa selenoprotein monoclonal antibody, binds substantially only to the 15 kDa selenoprotein, as described in Example 4, below.

Probes and primers: Molecules useful as nucleic acid probes and primers may readily be prepared based on the nucleic acids provided by this invention. Typically, but not necessarily, such molecules are oligonucleotides, i.e., linear nucleic acid molecules of up to about 100 nucleotides in length. However, longer nucleic acid molecules, up to and including the full length of the 15 kDa selenoprotein cDNA may also be employed for such purposes.

A nucleic acid probe comprises at least one copy (and typically many copies) of an isolated nucleic acid molecule of known sequence that is used in a nucleic acid hybridization protocol. Generally (but not always) the nucleic acid molecule is attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (In *Molecular Cloning: A Laboratory Manual*, Cold Spring Harbor, N.Y., 1989) and Ausubel et al. (In: *Current Protocols in Moleculr Biology*, Greene Publishing Associates and Wiley-Intersciences, 1987). Nucleic acid probes may be used in conjunction with array technologies to analyze the 15 kDa selenoprotein expression patterns in normal versus tumor cells. In this context, a number of probes that are generally not conjugated to a detectable label or reporter molecule are affixed to a surface and hybridized with a sample nucleic acid preparation.

Primers are short nucleic acids, usually DNA oligonucleotides 8–10 nucleotides or more in length, and more typically 15–25 nucleotides in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, Cold Spring Harbor, N.Y., 1989), Ausubel et al. (In: *Current Protocols in Molecular Biology*, Greene Publishing Associates and Wiley-lntersciences, 1987), and Innis et al., (*PCR Protocols, A Guide to Methods and Applications, Innis et al. (eds.), Academic Press, Inc., San Diego, Calif., 1990*). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the cDNA disclosed in Seq. I.D. No. 2 will anneal to a target sequence such as a homologous sequence in rat contained within a rat cDNA library with a higher specificity than a corresponding primer of only 15 nucleotides. Thus, in order to obtain greater specificity, probes and primers may be selected that comprise 20, 25, 30, 35, 40, 50, 75, 100 or more consecutive nucleotides of the 15 kDa selenoprotein cDNA or gene sequences.

The invention thus includes isolated nucleic acid molecules that comprise specified lengths of the disclosed transcription factor cDNA sequences. Such molecules may comprise at least 8–10, 15, 20, 25, 30, 35, 40, 50, 75, or 100 consecutive nucleotides of these sequences and may be obtained from any region of the disclosed sequences. By way of example, the human and mouse 15 kDa selenoprotein cDNAs shown in the Sequence Listing may be apportioned into halves or quarters based on sequence length, and the isolated nucleic acid molecules may be derived from the first or second halves of the molecules, or any of the four quarters. The human 15 kDa selenoprotein cDNA, shown in Seq. I.D. No. 2 may be used to illustrate this. This cDNA is 1244 nucleotides in length and so may be hypothetically divided into halves (nucleotides 1–622 and 623–1244) or quarters (nucleotides 1–311, 312–622, 623–933 and 934–1244). Nucleic acid molecules may be selected that comprise at least 8–10, 15, 20, 25, 30, 35, 40, 50, 75 or 100 consecutive nucleotides of any of these portions of the transcription factor cDNA. Thus, one such nucleic acid molecule might comprise at least 25 consecutive nucleotides of the region comprising nucleotides 1–1244 of the disclosed transcription factor cDNA.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Isolated: An "isolated" biological component (such as a nucleic acid or protein) has been substantially separated or purified away from other biological components in the cell of the organism in which the component naturally occurs, i.e., other chromosomal and extrachromosomal DNA and RNA and proteins. Nucleic acids and proteins which have been "isolated" thus include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified 15 kDa selenoprotein preparation is one in which the 15 kDa selenoprotein is more enriched than the protein is in its natural environment within a cell. Preferably, a preparation of 15 kDa selenoprotein is purified such that the 15 kDa selenoprotein represents at least 50% of the total protein content of the preparation.

Oligonucleotide: A linear polynucleotide sequence of up to about 100 nucleotide bases in length.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Therapeutically effective amount: A therapeutically effective amount of the 15 kDa selenoprotein is defined as an amount that decreases a subject's risk of developing cancer, caused by the subject's increased predetermined genetic susceptibility to cancer associated with a polymorphism in a 15 kDa selenoprotein gene. Administration of a therapeutically effective amount of the 15 kDa selenoprotein will result in an increased amount of the 15 kDa selenoprotein in the subject, as compared to the amount of 15 kDa selenoprotein present prior to the administration of the 15 kDa selenoprotein.

Mammal: This term includes both human and non-human mammals. Similarly, the terms "patient" and "subject" includes both human and veterinary subjects.

Amplify (amplifying, amplification): Increasing the concentration of a nucleic acid in a sample. One method will include the PCR reaction, which allows one to exponentially amplify the number of DNA molecules in a sample. Other methods may include, for example, dialysis. Other methods recognized by those skilled in the art are also included.

Tumor: Tumors are abnormal growths which can be either malignant or benign, solid or liquid (for example, hematogenous). This term particularly includes malignant tumors which can be either solid (such as a breast, liver, or prostate carcinoma) or liquid (such as a leukemia). Tumors can also be further divided into subtypes, such as adenocarcinomas (e.g. of the breast, prostate or lung).

Cancer: A malignant tumor.

II. Materials and Methods

A. Materials

[$^{75}$Se]Selenious acid was obtained from the Research Reactor Facility, University of Missouri (Columbia, Mo.), ECL systems from Amersham, EST clones from ATCC (#384717 from human placental cDNA library and #409024 from human infant brain cDNA library) and other reagents were commercial products of the highest grade available.

B. Methods

Standard molecular biology, biochemistry and immunology methods are used in the present invention unless otherwise described. Such standard methods are described in Sambrook et al. (In *Molecular Cloning: A Laboratory Manual*, Cold Spring Harbor, N.Y., 1989), Ausubel et al. (In: *Current Protocols in Molecular Biology*, Greene Publishing Associates and Wiley-Intersciences, 1987) and Harlow and Lane (*Antibodies, A Laboratory Manual*, Cold Spring Harbor Laboratory, New York, 1988).

DNA sequencing: Plasmids were isolated according to the instructions provided with the plasmid purification kit (Qiagen), the sequencing reaction products purified on separation columns as described by the manufacturer (Princeton Separations) and the nucleotide sequences of EST clones determined using a Dye Terminator Cycle Sequencing kit as described by the manufacturer (Perkin Elmer).

Computer analyses: Three different peptide sequences from the human 15 kDa selenoprotein were analyzed for matches to the dbEST database of partial cDNA sequences (Boguski et al., 1993, *Nature Genet.*, 4:332–3) using the BLAST (Altschul et al., 1990, *J. Mol. Biol.* 215:403–10 and Altschul et al., 1994, *Nature Genet.* 6:119–29) and gapped BLAST-2 (Altschul & Gish, 1996, *Methods Enzymol.* 266:460–80) programs. Multiple alignments of expressed sequence tag (EST) sequences and their translated products were viewed using the MSPcrunch/Blixem system (Sonnhammer & Durbin, 1994, *Comput. Appl. Biosci.*, 10:301–7). The Blixem alignments also revealed polymorphic sites in the human ESTs that were clearly distinct from sequencing errors.

Generation of Polyclonal Antibodies: Polyclonal antibodies which recognize the 15 kDa selenoprotein were made using standard procedures (for example Harlow and Lane, Antibodies: A laboratory manual, Cold Spring Harbor Laboratory, 1988, Chapter 5). A synthetic peptide fragment containing the C-terminal region of Seq. I.D. No. 1 (amino acids 145–162) was conjugated to the carrier KLH (keyhole limpet hemacyanin) and injected into rabbits. Specificity of the polyclonal antisera was determined using Western blotting of the purified recombinant human 15 kDa selenoprotein.

III. Purification and Characterization of the Human 15 kDa Selenoprotein

The human 15 kDa selenoprotein was detected in and purified from the human Jurkat T-cell line, JPX9 (Nagata et al., 1989, *J. Virol.* 63:3220–6) by growing the cells in the presence of $^{75}$Se followed by analysis of extracts of the $^{75}$Se-labeled cells by SDS PAGE and PhosphorImager detection of radioactivity on the gels. One of the major $^{75}$Se-labeled proteins that migrated as a 15 kDa band on SDS PAGE was purified initially on DEAE-Sepharose and phenyl-Sepharose columns, and then further on a reverse-phase column. The procedures used were as follows. JPX9, was grown and labeled with [$^{75}$Se]selenious acid (2 μCi/ml) as described in Gladyshev et al. (*Proc. Natl. Acad. Sci. USA* 93:6146–51, 1996). $^{75}$ Se-labeled JPX9 cells were mixed with unlabeled cells, suspended in 2 volumes of 30 mM Tris-HCl, pH 7.5, 1 mM EDTA, 2 mM DTT, 1 mM MgCl$_2$, 1 mM phenylmethylsulfonyl fluoride and disrupted by sonication. Disrupted cells were centrifuged, the supernatant applied to a DEAE-Sepharose column, which had been equilibrated with 30 mM Tris-HCl, pH 7.5, 2 mM DTT and 1 mM EDTA (buffer A), the column washed with 2 volumes of buffer A and proteins eluted by application of a linear gradient from 0 to 500 mM NaCl in buffer A. Fractions containing $^{75}$Se were analyzed on SDS gels. Fractions containing the human 15 kDa selenoprotein that eluted from the DEAE column with 350 mM NaCl were combined, concentrated, adjusted to a concentration of 0.5 M ammonium sulfate in buffer A, applied to a phenyl-Sepharose column equilibrated in 1 M ammonium sulfate in buffer A, the column washed by application of a linear gradient from 0.5 to 0 M ammonium sulfate in buffer A, and radioactive fractions corresponding to the 15 kDa selenoprotein eluted by application of a linear gradient from buffer A to water. Radioactive fractions were combined, concentrated, and loaded on a C$_{18}$ reverse-phase HPLC column that had been equilibrated in 0.05% trifluoroacetic acid (TFA), a gradient of 0 to 60% acetonitrile in 0.05% TFA applied and $^{75}$Se-containing fractions corresponding to the 15 kDa selenoprotein eluted at 48% acetonitrile.

Fractions containing the human 15 kDa selenoprotein from the C$_{18}$ column were dried on a Speed-Vac SC110 (Savant), dissolved in SDS-PAGE sample buffer and analyzed by SDS-PAGE. The molecular mass of the human 15 kDa selenoprotein was determined by electrospray and MALDI mass-spectrometry in fractions from the C$_{18}$ column. Both mass spectra revealed a single strong signal of the 15 kDa selenoprotein. The native molecular mass of the 15 kDa selenoprotein purified on a DEAE-Sepharose column was determined using native PAGE and analytical HPLC gel filtration as described by Gladyshev et al. (*Biochemistry* 35:213–23, 1996). The 15 kDa selenoprotein was detected as $^{75}$Se-labeled fractions from a gel-filtration column and as a $^{75}$Se-labeled band on native PAGE.

The molecular mass of the human 15 kDa selenoprotein subunit in fractions from the C$_{18}$ column determined by MALDI mass-spectrometry was 14,830 Da. Electrospray mass-spectrometry of the same preparation revealed a molecular mass of 14,870 Da. The N-terminus of the protein was blocked which prevented determination of the N-terminal sequence.

Amino acid analysis of the purified protein (performed by Harvard Microchem, Boston, Mass.), shown in Table 1, reveals a lack of internal methionine and histidine residues, as well as the hydrophobic character of the protein.

TABLE 1

Amino acid composition of the human 15 kDa selenoprotein

| Amino Acid | 162 Residues | 135 Residues | Experimental Data |
| --- | --- | --- | --- |
| A | 13 | 8 | 9.1 |
| R | 8 | 7 | 6.5 |
| N | 5 | 5 | ND |
| D | 8 | 8 | ND |
| C | 8 | 7 | ND |
| E | 13 | 13 | ND |
| Q | 8 | 7 | ND |
| G | 13 | 10 | 12.9 |
| H | 0 | 0 | <0.5 |
| I | 5 | 5 | 5.0 |
| L | 26 | 20 | 19.2 |
| K | 9 | 9 | 9.3 |
| M | 1 | 0 | <0.5 |
| F | 10 | 9 | 7.5 |
| P | 6 | 4 | 5.0 |
| S | 13 | 11 | 11.4 |
| T | 3 | 2 | 3.2 |
| W | 1 | 1 | ND |
| Y | 2 | 2 | 2.7 |
| V | 9 | 6 | 6.7 |
| U | 1 | 1 | ND |
| E + Q | 21 | 20 | 21.4 |
| D + N | 13 | 13 | 14.6 |

The 162 residue sequence corresponds to a full size open reading frame.
The 135 residue sequence corresponds to the open reading frame after removal of 27 N-terminal residues. U represents selenocysteine.

IV. Characterization of Human 15 kDa Selenoprotein cDNA and Polypeptide Sequences The sequences of three different tryptic peptides and one overlapping peptide from the 15 kDa selenoprotein were determined. Computer searches of the partial cDNAs in the expressed sequence tags database (dbEST) using TBLASTN program revealed nucleotide sequences that corresponded to all three peptides in the same OPF. These cDNA sequences were used to assemble an open reading frame, depicted in FIG. 1. The two cDNA clones containing the longest 5' sequences were obtained from I.M.A.G.E. Consortium at the Lawrence Livermore National Laboratory (California) (http://www-bio.llnl.gov/bbrp/image/image.html) and sequenced. These clones revealed a continuous nucleotide sequence of 1268 nucleotidesi containing a single open reading frame of 162 amino acid residues and a 3'-end polyA tail. A single ATG codon occurs in a nucleotide context, GCG<u>ATG</u>G, that is similar to the Kozak consensus sequence for initiation of translation (Kozak, 1997, EMBO J. 16:2482–92). This initiation ATG codon is followed by a 489 nucleotide open reading frame with an in-frame TAA termination codon. The obtained ORF includes an in-frame TGA codon, suggesting the presence of a selenocysteine residue, Sec93. Three tryptic peptides for which sequences have been determined correspond to deduced sequences located downstream of the TGA codon, indicating readthrough of the TGA codon, rather than termination of translation. Although selenocysteine was not directly identified as a component of the 15 kDa selenoprotein, the labeling of the protein with $^{75}$Se, readthrough of the TGA codon and the location of selenocysteine insertion sequence (SECIS) element in the untranslated area (below) suggest the presence of selenocysteine in the protein. The predicted ORF encoded a protein of 17,790.6 Da. The mass of the purified 15 kDa selenoprotein was 14,870 Da, and this discrepancy suggested post-translational processing of the protein. Processing of the 15 kDa selenoprotein appears to occur at the N-terminal portion of the protein. Since antiserum raised to a synthetic peptide that was identical in sequence to the eighteen C-terminal residues of the 15 kDa selenoprotein, it recognized the 15 kDa selenoprotein at different stages of purification. In addition, one of the sequenced tryptic peptides obtained from digests of the 15 kDa selenoprotein corresponded to residues 146–158, located near the C-terminus according to the predicted gene sequence.

The N-terminal portion of the putative precursor of the 15 kDa selenoprotein, as predicted from the gene sequence, has a stretch of hydrophobic amino acid residues, suggesting the presence of a signal peptide. Cleavage of these N-terminal amino acid residues is consistent with the amino acid composition of the protein (Table 1), since the processed protein matches more closely the amino acid analysis data obtained for the purified 15 kDa selenoprotein than the full size 17 kDa protein. One possible site for post-translational processing is Ser27, which coincides with the site of an exon-intron junction (not shown), making this residue the evolutionary favorable site for post-translational processing.

Homologous Mouse, Rat, *Brugia malayi*, *Caenorhabditis elegans* and Rice Gene Sequences Computer sequence analyses of the 15 kDa selenoprotein and its gene sequence revealed no homology to known proteins. However, a number of dbEST sequences from mouse, rat, *B. malayi, C. elegans* and rice showed strong homology in TBLASTN searches with the 15 kDa human protein (FIG. 2).

The amino acid sequence of the mouse protein was deduced from the assembly of 39 independent partial cDNA sequences in dbEST. In addition, experimental confirmation of the 5' region encoding the mouse N-terminal sequence was made from partial cDNAs obtained from the IMAGE consortium. The *C. elegans* sequence was assembled from two partial cDNA clones (GenBank dbEST accession numbers C10051 and C08344) which are identical for an 81 bp region of overlap and encode the apparently complete reading frame shown. The partial amino acid sequence of the homolog from the filarial nematode, *B. malayi*, was translated from a single partial cDNA (GenBank dbEST accession number AA257328). Two rice partial eDNAs (GenBank dbEST accession numbers D47693, D47819) covered the translated region shown (in addition, shorter segments of similarity to the human sequence were noted in translations further downstream, but these were in error-prone regions of mismatch between the two ESTs and are not shown). All pairwise alignments were strongly significant, as shown by TBLASTX-2 (Washington University gapped blast, February 1997 release obtained from http:J/blast.wustl.edu/blast/executables). Typical EST pairs gave amino acid gapped E (expect) values (BLOSUM 62 matrix), using the sum statistics of Altschul and Gish (*Methods Enzymol.* 266:460–80, 1996) as follows (with the highest HSP score appended in parentheses): human/mouse: $2\times10^{-35}$ [717]; human/*C. elegans*: $2\times10^{-20}$ [252]; human/*B. malayi*: $8\times10^{-12}$ [228]; *C. elegans*/*B. malayi*: $8\times10^{-21}$ [257]; human/rice (including multiple short matches for scoring purposes): $1\times10^{-2}$ [82].

Interestingly, although mouse and rat genes encode potential selenocysteine-containing 15 kDa proteins, the genes in *C. elegans* and *B. malayi* encode homologous proteins containing cysteine in place of selenocysteine. This is consistent with observations that nematode genes for glutathione peroxidase and thioredoxin reductase encode cysteine analogs of mammalian selenocysteine-containing proteins. The complete mouse 15 kDa selenoprotein cDNA and amino acid sequences are presented in Seq. I.D. Nos. 8 and 9, respectively.

The regions flanking Sec93 in the human 15 kDa selenoprotein had the highest degree of homology among proteins from different organisms, suggesting that the selenocysteine residue is located in a putative active center. In other mammalian selenocysteine-containing proteins, in which the function is established, the selenocysteine residue is located at the active center and it is essential for catalytic activity of the selenoenzyme (Stadtman, 1996, *Annu. Rev. Biochem.* 65:83).

VI. Tissue Distribution of the Human 15 kDa Selenoprotein

Approximately 120 partial human cDNA sequences in dbEST were found to match the human 15 kDa selenoprotein DNA sequence (within experimental error or expected frequencies of natural polymorphism). This sampling represents a sufficient abundance of independent clones to reveal the approximate tissue distribution of expression of this relatively highly-expressed gene (expression as mRNA). cDNA libraries from 32 different adult, fetal or embryonic tissues or organs were represented in this set of sequences. Table 2 shows the ranked incidence of these clones in tissues and organs for which at least one library has two or more independent 15 kDa selenoprotein cDNAs in dbEST.

Clearly, the 15 kDa selenoprotein gene exhibits a very broad spectrum of moderate expression in many tissues, and significantly higher levels of mRNA are shown by thyroid, parathyroid tumor, prostate and pre-cancerous prostate cells. Expression estimates from dbEST library frequencies should be considered to be only semi-quantitative, considering that some libraries are normalized and variable levels of tissue contamination may exist. More quantitative representative estimates are given by the stringent CGAP (Cancer Gene Anatomy Project) libraries (Strausberg et al., 1997, *Nature Genet.* 15:415–6) prepared from small numbers of laser-microdissected cells, for example the pre-cancerous prostate library CGAP_Pr2 (Krizman et al., 1996, *Cancer Res.* 56:5380–3; Table 2). Irrespective of the quantitative uncertainties, this large body of partial cDNA sequence data strongly demonstrates that the 15 kDa protein gene is expressed in a wide range of human tissues, with increased levels of mRNA in the thyroid, parathyroid and prostate-derived cells. The expression of the mouse analog of the human 15 kDa selenoprotein was examined by immunoblot assays in prostate, heart, kidney, spleen, liver and other mouse organs, with the highest level observed in prostate, suggesting the expression of both mRNA and the selenoprotein in many tissues and cell lines.

TABLE 2

Incidence of the human 15 kDa selenoprotein gene expression

| Library | Incidence per 10,000 ESTs (numbers/library size) |
| --- | --- |
| Thyroid | 19.9 (4/2014) |
| Parathyroid tumor (Soares NbHPA) | 18.4 (12/6511) |
| Prostate pre-cancerous cells (CGAP_Pr2) | 15.4 (3/1945) |
| Prostate | 11.2 (2/1792) |
| Fetal lung (Soares NbHL19W) | 9.8 (9/9145) |
| Colon carcinoma (3 libraries) | 5.6 (2/3358, 1/2791, 1/956) |
| Aorta | 4.4 (2/4595) |
| Fetal retina (Stratagene 937202) | 4.3 (2/4610) |
| Jurkat T-cells (2 libraries) | 4.3 (2/3534, 1/3420) |
| Retina (2 libraries) | 4.1 (3/8915, 2/3368) |
| Neuroepithelium (Stratagene 937231) | 3.7 (2/5385) |
| Colon (Stratagene 937204) | 3.3 (3/8974) |
| Testis (Soares NHT) | 2.9 (4/13657) |
| Fetal heart (Soares NbHH19W) | 2.3 (6/25708) |
| Germinal B-cells (CGAP_GCB1) | 1.0 (2/19194) |

17 libraries from other tissues, including 3 distinct embryo libraries, contained only a single 15 kDa protein cDNA clone and are not tabulated here. For some clones, both 5' and 3' EST sequences are present in dbEST: these count as only a single cDNA in these calculations.

VII. Selenocysteine Insertion Element Sequence

Studies of the mechanism of selenocysteine incorporation into several eukaryotic selenoproteins have implicated related stem-loop structures, located in the mRNA 3'UTR, as essential for selenocysteine insertion into proteins at a UGA codon in the coding sequence. The general structural features of this SECIS (selenocysteine insertion sequence) element have been deduced previously (Low and Berry, 1996, *Trends Biochem. Sci.* 21:203, and Walczak et al., 1996, *RNA*, 2:367), based on chemical probe experiments and sequence alignments, as summarized in FIG. 3.

To locate potential SECIS elements in the 15 kDa selenoprotein mRNAs, the human and mouse cDNAs were searched for sequences meeting the following constraints (see FIG. 3A): Helix 1: at least 4 base pairs; Internal loops: 3–9 nucleotides; Quartet (the non-Watson-Crick base paired motif): UGAN (following A in Internal loop) NGAN (following the downstream strand of Helix II); Helix II: 9–15 standard base pairs extending the Quartet; Apical loop: 10–20 nucleotides starting with AA(A/G). Single base mismatches or bulges were allowed within helices longer than 6 base pairs.

Sequences meeting these stringent criteria were found in both the human and mouse 3'-UTRs, ending approximately 60 nucleotides upstream of the poly-A addition signal sequence (FIG. 1). FIG. 3B shows these human and mouse sequences aligned with the canonical SECIS element (Low and Berry, 1996, *Trends Biochem. Sci.* 21:203, and Walczak et al., 1996, *RNA* 2:367) of the human glutathione peroxidase 1 (GPX-1) mRNA 3'-UTR The 15 kDa protein mRNAs exhibit all the features known to be necessary in other eukaryotic selenoprotein mRNAs to promote selenocysteine insertion.

VIII. Chromosomal Localization of the Gene for the 15 kDa Selenoprotein

Computer analyses revealed the UNIGENE cluster of ESTs (Boguski and Schuler, 1995, *Nature Genetics* 10:369–371) corresponding to the 15 kDa human selenoprotein maps to human chromosome 1, at the position 117–123 cM on the human transcript gene map, corresponding approximately to 1p31 (Schuler et al., 1996, *Science* 274:540–6).

IX. Differential Expression of the 15 kDa Selenoprotein Polypeptide and mRNA in Cancers The expression of the 15 kDa selenoprotein and its mRNA is altered in several mouse and human cancers compared to non-cancerous tissues. Variations in the levels of both the polypeptide and the mRNA can be detected using standard procedures such as Western blotting (for polypeptide) and Northern blotting (mRNA).

For example, the expression of the 15 kDa selenoprotein was compared in cancerous and non-cancerous mouse liver tissues by Western blotting using the polyclonal antibody described above. As shown in FIG. 4, equal amounts of protein were loaded on each lane in the following order: lanes 1 and 2, wild type, 2.5 months; lanes 3 and 4-c-myc, 2.5 months; lanes 5 and 6-c-myc/TGFα, 2.5 months; lanes 7 and 8-c-myc/TGFα, 10 months; lanes 9–11-c-myc/TGFα, tumor, 10 months; lanes 12 and 13-wild type, 1 month; lanes 14 and 15-c-myc, 1 month; lanes 16 and 17-c-myc/TGFα, 1 month; lanes 18 and 19-c-myc/TGFα, 10 months; lanes 20–22-c-myc/TGFα, tumor, 10 months. Each sample is from a different mouse. c-myc/TGFα represents a double transgenic mouse. The c-myc and c-myc/TGFα mice are models for accelerated hepatocarcinogenesis.

The levels of the 15 kDa selenoprotein polypeptide were observed to be 3–5 fold lower in tumor than in surrounding tissue in livers of c-myc/TGFα transgenic mice (FIG. 4). These mice are characterized by elevated production of reactive oxygen species, increased lipid peroxidation and significant chromosome abnormalities. Oxidative stress in c-myc/TGFα mice can be reduced by supplementation of the diet with vitamin E (V. Factor, personal communication), suggesting that selenium may have a similar protective effect. On the other hand, expression of the 15 kDa protein was not altered in hepatocarcinomas of c-myc and c-myc/TGFβ transgenic mice, for which no oxidative stress has been reported.

Additionally, Western blotting also revealed decreased expression of the 15 kDa selenoprotein in prostate cancer cell lines relative to the normal prostate (see FIG. 5). Equal protein amounts were loaded on each lane as follows: lane 1-c-myc/TGFα liver, 10 months (matched to the sample in lane 2); lane 2-c-myc/TGFα liver, tumor 10 months; lane 3-mouse prostate; lane 4-purified human T-cell 15 kDa protein control 1; lane 5-mouse prostate cancer cell line 1; lane 6-mouse prostate cancer cell line 2; lane 7-mouse prostate; lane 8-c-myc/TGFα liver, 10 months (matched to the sample in lane 9); lane 9-c-myc/TGFα liver, 10 months; lane 10-purified human T-cell 15 kDa protein control 2.

Northern blotting revealed decreased expression of the human 15 kDa selenoprotein mRNA in matched samples from lymphoma and ovarian and fallopian tube cancers, and corresponding normal lymph node, ovary and fallopian tube (data not shown).

X. Tumor-Related Variants in the 15 kDa Selenoprotein SECIS Element

Figure 6:
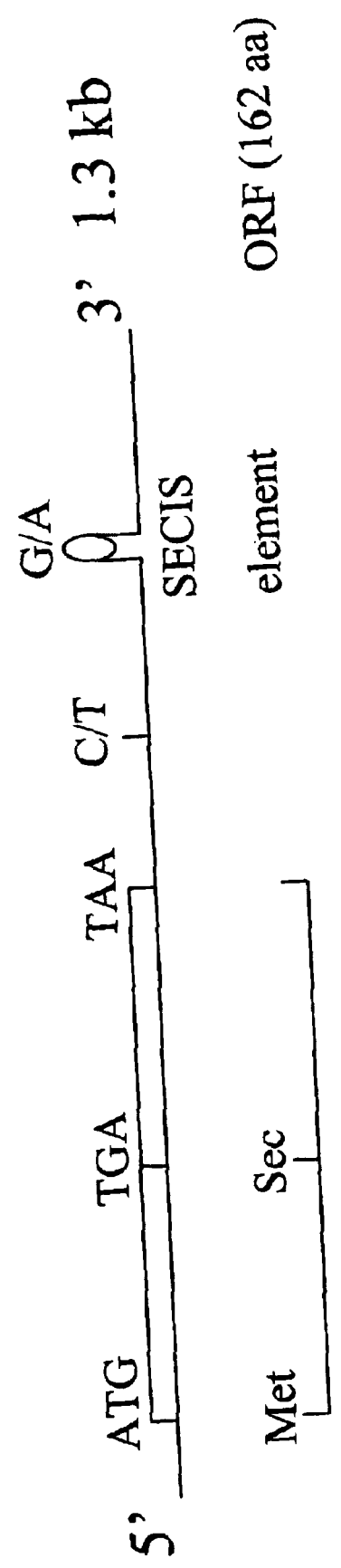
FIG. 6 is a representative drawing showing the structure of the human 15 kDa selenoprotein cDNA. The C/T and G/A polymorphisms at nucleotide positions 811 and t 125 respectively, are shown.

Human EST alignments indicated that a G/A substitution polymorphism or mutation (FIG. 6) occurred at an apical loop nucleotide of the SECIS element in the 3'-UTR region of the human 15 kDa selenoprotein cDNA sequence (nucleotide position 1125). An additional substitution (C/T) polymorphism was observed at position 811 (FIG. 6). Sequence analysis of the region containing the polymorphisms for over 100 individuals revealed that the substitution polymorphisms at these two variant sites, positions 811 and 1125, were linked to each other with a very high probability. Only two variations of the polymorphisms were detected. Individuals with a C at position 811 always had a G at position 1125 (form 1: C811 . . . G1125, referred to herein as CG), while individuals with a T at position 811 always had an A at position 1125 (form 2: T811 . . . A1125, referred to herein as TA).

Given the critical role that the SECIS element has in incorporation of selenocysteine into proteins, changes in nucleotide 1125 located in the SECIS element may affect the efficiency of selenocysteine incorporation in the coding region of the gene, thereby providing a mechanism for controlling the expression of the 15 kDa selenoprotein in tumor and normal tissues.

The genotype of the 15 kDa selenoprotein was determined for several individuals. Normal and cancerous tissues were collected, as well as blood samples to determine if the genotype of the tumor was different from that of non-tumor lymphocytes within the same individual. DNA from the blood and tissue samples was isolated using the protocols and procedures included in the Puragene DNA Isolation Kit (Gentra). The isolated DNA (0.1–1.0 µg) was used as template for Polymerase Chain Reaction (PCR) amplification using the GeneAmp PCR Amplification Kit and the following primers: forward primer 5'-CAGACTTGCGGTTAATTATG-3' (Seq. I.D. No. 12) and the reverse primer 5'-GCCAAGTATGTATCTGATCC-3' (Seq. I.D. No. 13). The PCR reactions included 0.2 mM dNTPs, 1.5 mM MgCl$_2$, 0.4 mM each primer and 1.25 units of Taq polymerase and were incubated for 35 cycles of 85° C. for 30 seconds, 45° C. for 60 seconds, 72° C. for 90 seconds). Successful amplification was indicated by the appearance of a DNA band of approximately 400 bp on a 1% agarose gel. The resulting PCR product was subjected to primer extension or restriction digestion, to determine the genotype of the individual.

To determine the nucleotide identity at position 811 or 1125 within the human 15 kDa selenoprotein gene by primer extension, radioactive primers were used. For the determination of the nucleotide at position 811 the primer used was 5'-GGCATAGTAATCATCTGTCTTGTT-3' (Seq. I.D. No. 14), while the primer 5'-GTATGTATCTGATCCACACAAATCC-3' (Seq. I.D. No. 15) was used to determine the nucleotide at position 1125. The primers were radiolabeled by 5'-end labeling with gamma-labeled ATP and polynucleotide kinase. Labeled primer and DNA were mixed in a solution of 40 mM Tris HCl (pH 7.5), 20 mM MgCl$_2$ and 50 mM NaCl, heated to 95° C. for 10 minutes, then transferred to a 37° C. water bath for 1 hour. Extension was accomplished by the addition of 5 µl of a solution containing 100 mM DTT, 1 mM each of 3 dNTPs, 5 mM dideoxynucleotide triphosphate, and 5 units of reverse transcriptase or T7 polymerase. The mixture was further incubated for 15 minutes at 42° C., ethanol precipitated, resuspended in formamide loading buffer and the extension products separated on a 10% polyacrylarmide gel. Visualization of the extension products was accomplished by autoradiography or phosphorimaging.

Figure 7A:
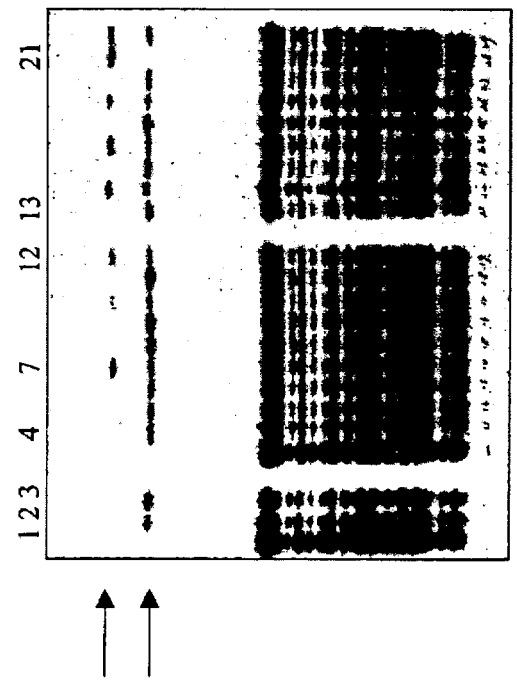
FIG. 7 is a digital image showing the use of primer extension (A) and restriction digestion (B and C for the detection of polymorphisms, to determine an individual's genotype.

FIG. 7A shows the results of using primer extension with ddGTP to examine the polymorphism at position 811. The arrows show the primer extension products corresponding to two polymorphic forms, C (lower arrow) or T (upper arrow) at position 811. DNA from head and neck tumors was PCR amplified, isolated, and primer extended using Seq. I.D. No. 14. The first lane contains primer only. Lanes containing only the lower, shorter band are samples that are homozygous for C at position 811 (for example lanes 2–6). Lanes containing only the upper, longer band are samples that are homozygous for T at position 811 (lane 21). Finally, lanes containing both the lower and upper band are samples that are heterozygous (CT) at position 811 (for example lanes 7, 10, 12).

Although primer extension successfully allows for the determination of the genotype of the 15 kDa selenoprotein gene, the method is time consuming and requires the use of radioactive compounds. Therefore, an alternative method to determine the nucleotide identity at positions 811 and 1125 within the human 15 kDa selenoprotein gene was developed using restriction enzyme digestion. The PCR amplified DNA generated above (0.5 µg) was digested with DraI (recognition sequence TTTAAA, Pharmacia), to evaluate the nucleotide identity at position 811, or digested with BfaI (recognition sequence CTAG, New England Biolabs), to identify the nucleotide at position 1125, using buffers and conditions provided by the respective vendors. Evaluation of whether the DNA was digested was accomplished by gel electrophoresis in 1% agarose.

Figure 7C:
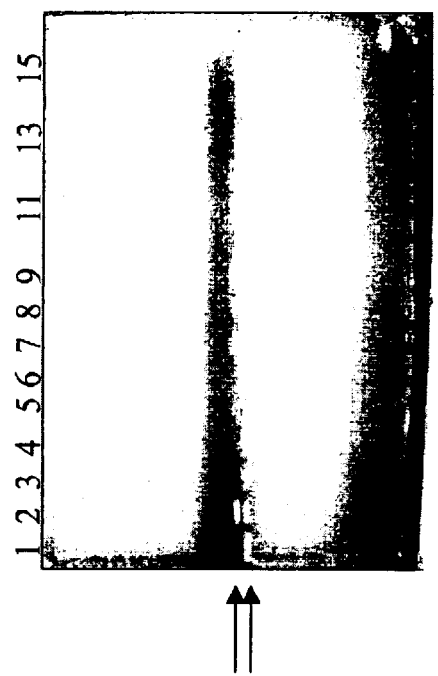
Figure 7B:
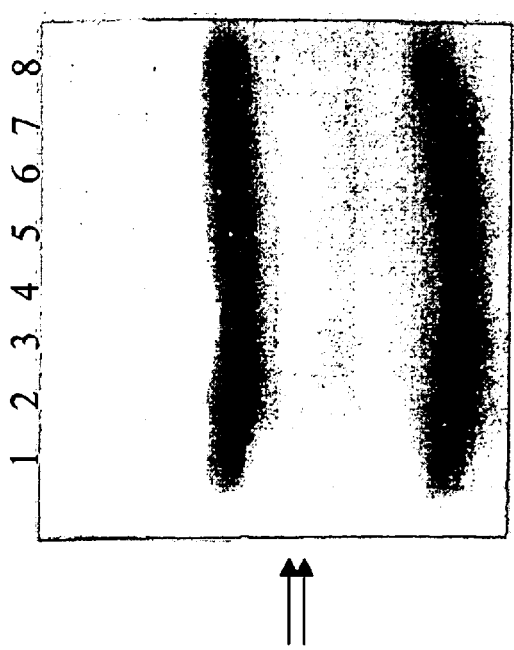

As shown in FIGS. 7B and C, restriction digestion can be used to determine the genotype of the 15 kDa selenoprotein gene. FIG. 7B shows DNA digested with DraI to identify the nucleotide at position 811. Only DNA containing a T at position 811 will be digested. Therefore, lanes containing only the upper band (lanes 2, 5, 6) are from individuals homozygous C at position 811 (compare to lane 8, undigested DNA). Lanes containing only the lower band (lane 4) are from individuals homozygous T at position 811 (both stands of DNA cut). Lanes containing both bands (lanes 1, 3, 7) are from individuals heterozygous (C/T) at position 811. The same analysis is used for FIG. 7C, which shows DNA digested with BfaI to identify the nucleotide at position 1125. Only DNA containing a G at position 1125 will be digested. Lanes containing only the upper band are homozygous A (neither strand of DNA cut), lane containing only the lower band are homozygous G (both strands of DNA cut), while lanes containing both bands are heterozygous G/A at position 1125.

The experiments described above verified both the existence of polymorphisms at nucleotide positions 811 and 1125 within the 15 kDa selenoprotein gene, and the ability to determine an individual's genotype with respect to the 15 kDa selenoprotein gene. Using these methods, the correlation between the polymorphisms at positions 811 and 1125 in the 15 kDa selenoprotein gene and incidence of cancer, as well as race, was determined. The genetic distribution of alleles was analyzed in more than 200 human normal and tumor samples (Table 3). DNA from normal tissue, head and neck tumors, and colon tumors was isolated and amplified using PCR as described above with primers shown in Seq. I.D. Nos. 12 and 13. The PCR product was restriction digested with DraI, to determine the nucleotide identity at position 811 or BfaI, to determine the nucleotide identity at position 1125.

The differences in genotype between control and cancer patients was examined, as well as the differences between Caucasian and African Americans (blacks or persons of African ancestry). CG/CG and TA/TA patients are homozygous at positions 811 and 1125 and CG/TA patients are heterozygous at positions 811 and 1125. As shown in Table 3, the presence of the substitution polymorphisms, T substituted for C at position 811 and A substituted for G at position 1125, were found more often in cancer samples, and is designated as a "cancer" polymorphism. The cancer polymorphism therefore includes both the CG/TA and TA/TA alleles in Table 3. The tendency of the cancer polymorphism to be present in individuals having cancer was observed for the Caucasian population, and this observation was statistically significant for the African American population. Table 3 also demonstrates that the cancer polymorphism is more prevalent in the African American population. In addition, an example of loss of heterozygosity has been detected in the sample of African American origin. The African American population is known to be at higher risk of prostate cancer and dietary selenium (which may increase expression of the 15 kDa selenoprotein) has the single most pronounced effect in preventing this particular type of cancer. The high expression of the 15 kDa protein in prostate tissue correlates with both the chemopreventive effect of selenium in the prostate, and the increased risk of prostate cancer in the African American population. Therefore, determination of an individual's genotype may be used as an indicator of the need for dietary selenium supplementation to inhibit tumor development.

These data suggest that patients containing the allele with the cancer polymorphism are more likely to develop cancer. Therefore, this cancer polymorphism may be used as the cancer predicting tool for populations at risk for developing certain cancers.

TABLE 3

Genotype analysis of the 15 kDa selenoprotein polymorphisms

|  | CG/CG | CG/TA | TA/TA |
|---|---|---|---|
| Caucasians |  |  |  |
| Normal | 19 (58%) | 13 (39%) | 1 (3%) |
| Head and Neck Cancer | 34 (57%) | 21 (35%) | 5 (8%) |
| Colon Cancer | 11 (50%) | 9 (41%) | 2 (9%) |
| Colon cancer patients lymphocytes | 9 (53%) | 6 (35%) | 2 (12%) |
| African Americans |  |  |  |
| Normal | 11 (17%) | 37 (59%) | 15 (24%) |
| Head and Neck Cancer | 7 (24%) | 11 (38%) | 11 (38%) |
| Colon Cancer | — | — | 1 |

XI. Expression of Recombinant 15 kDa selenoprotein in E coli.

Figures 8A, 8B:
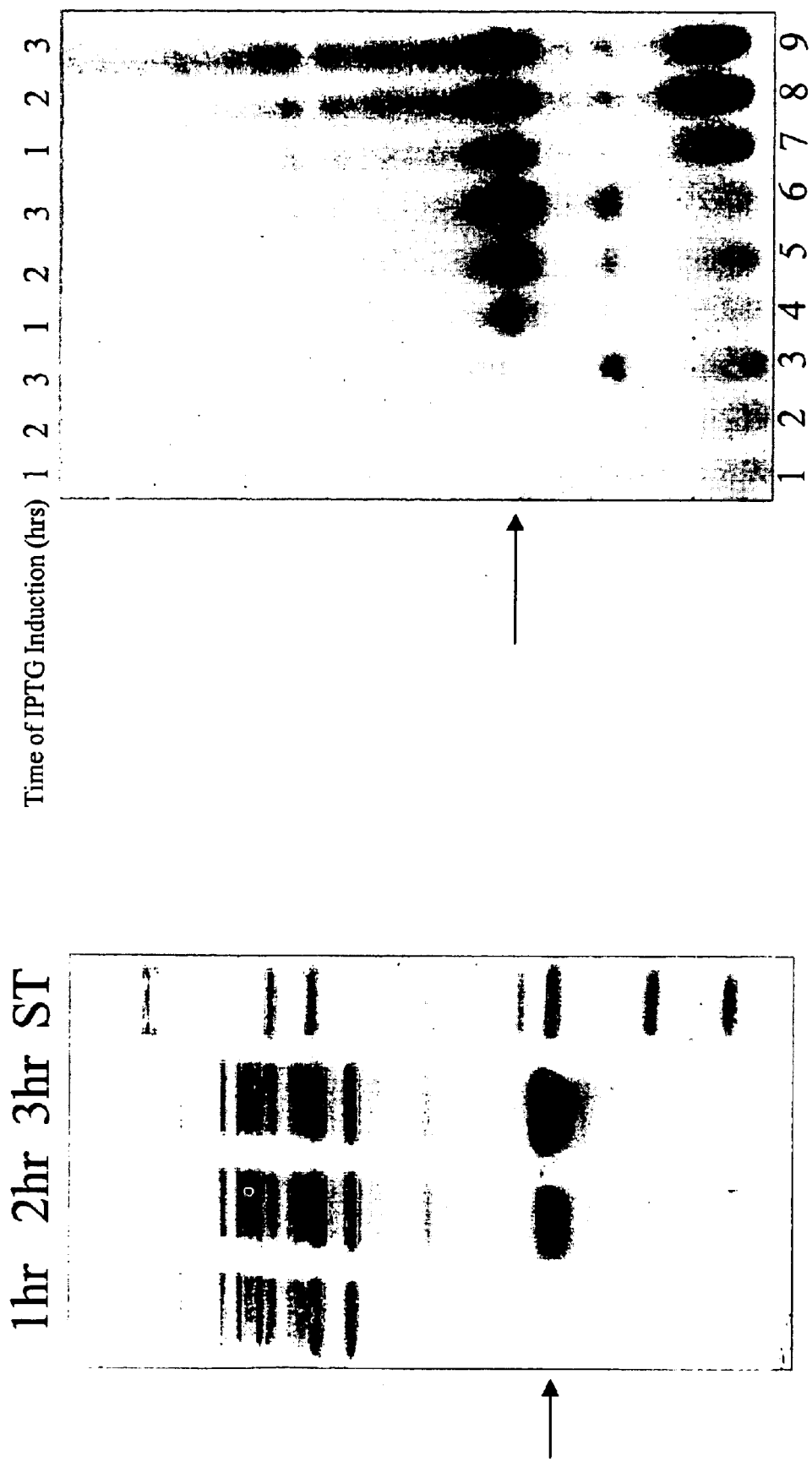
FIG. 8A is a digital image showing the expression of recombinant forms of the 15 kDa selenoprotein, with Coomassie Blue staining showing the overexpression of the His-tag cysteine-for-selenocysteine mutant form of the 15 kDa selenoprotein.
FIG. 8B is a digital image showing expression of the His-tag selenocysteine-containing form of the 15 kDa selenoprotein. Lanes 1–3: 15 kDa selenoprotein cDNA; lanes 4–9: selenocysteine insertion sequence elements constructed downstream of TGA encoding selenocysteine (see FIGS. 9B and C). Selenium-containing proteins were detected by metabolic labeling with $^{75}$Se and visualized with a PhosphorImager.

The human 15 kDa selenoprotein was expressed in BL21 (DE3) *E. coil* in the form of its cysteine-for-selenocysteine mutant (T for A substitution at nucleotide position 283), with (FIG. 8A) and without a His-tag using the pET-21b(+) vector (Novagen). Bacteria were grown in LB media with 100 mg/liter ampicillin at 37° C. to $OD_{600}$=0.5, then induced with 1 mM IPTG. Growth was continued for 3 hours at 37° C. after induction. As shown in FIG. 8A (arrow), high-levels of the cysteine mutant are expressed 3 hours after IPTG induction.

In addition, the human 15 kDa selenoprotein was genetically engineered to design a bacterial selenocysteine insertion sequence element (stem-loop structure downstream of the selenocysteine TGA codon), so that selenocysteine would be incorporated into the human 15 kDa selenoprotein during its expression in bacteria. (FIGS. 8B and 9). The nucleotide sequence downstream of TGA (encoding selenocysteine) was mutated in such a way that the mRNA structure would be formed that resembles the mRNA structure in the *E. coli* formate dehydrogenase H that is necessary for selenocysteine incorporation (FIG. 9A). Two different constructs were generated (FIGS. 9B and C), containing mutations in the area downstream of TGA. These mutants had a protein sequence that was different in either 3 or 4 amino acid residues from the wild type human 15 kDa selenoprotein sequence.

$^{75}$Se-labeling experiments (1 nmol/ml radioactive $Na_2^{75}SeO_3$ (~8 Ci/nmol) was added at the time of IPTG induction, as described above) demonstrated that the designed mRNA structure resulted in selenocysteine incorporation into protein (FIG. 8B). Thus, the recombinant 15 kDa selenoproteins will be available for functional studies as described in the examples below (for example, generating antibodies as in Example 4). This is the first time any mammalian selenoprotein was expressed in bacteria in a form that contains a selenocysteine residue.

EXAMPLES

The following examples are illustrative of the scope of the present invention.

Example 1

Obtaining 15 kDa Selenoprotein cDNA

The foregoing discussion describes the original means by which the complete human and mouse 15 kDa selenoprotein cDNAs were obtained and provides the nucleotide sequence of these cDNAs. With the provision of this sequence information, the polymerase chain reaction (PCR) may now be utilized in a more direct and simple method for producing this cDNA.

To amplify the human or mouse 15 kDa selenoprotein cDNA sequences, total RNA is extracted from human or mouse cells (e.g., hepatocytes) and used as a template for performing the reverse transcription-polymerase chain reaction (RT-PCR) amplification of cDNA. Methods and conditions for RT-PCR are described in Kawasaki et al. (In *PCR Protocols, A Guide to Methods and Applcations*, Innis et al. (eds.), 21–7, Academic Press, Inc., San Diego, Calif., 1990). The selection of PCR primers is made according to the portions of the cDNA which are to be amplified. Primers may be chosen to amplify small segments of a cDNA or the entire cDNA molecule. Variations in amplification conditions may be required to accommodate primers of differing lengths; such considerations are well known in the art and are discussed in Innis et al. (*PCR Protocols, A Guide to Methods and Applications*, Innis et al. (eds.), Academic Press, Inc., San Diego, Calif., 1990). For example, the open reading frame of the human 15 kDa selenoprotein cDNA may be amplified using the following combination of primers: primer H1 5' ATGGCGGCTGGGCCGAGTGGG 3' (Seq. I.D. No. 5) and primer H2 5' TAATATGCGTTC-CAACTTTTC 3' (Seq. I.D. No. 6), whereas that portion of the cDNA encoding the putative mature protein may be amplified using the following combination of primers: primer H3 5' TCTGCTTTTGGGGCAGAGTTT 3' (Seq. I.D. No. 7) and primer H2 5' TAATATGCGTTC-CAACTTTTC 3' (Seq. I.D. No. 6).

Similarly, the open reading frame of the mouse 15 kDa selenoprotein cDNA may be amplified using the following combination of primers: primer M1 5' ATGGCG-GCAGGGCAGGGTGGG 3' (Seq. I.D. No. 10) and primer M2 5' TATGCGTTCCAACTTCTCGCT 3' (Seq. I.D. No. 11).

These primers are illustrative only; it will be appreciated by one skilled in the art that many different primers may be derived from the provided cDNA sequences in order to amplify particular regions of the cDNAs.

Alternatively, the gene sequences corresponding to the cDNA sequences presented herein (i.e. the genomic sequence including introns) or pieces of such gene sequences may be obtained by amplification using primers based on the presented cDNA sequences using human or murine genomic DNA as a template.

PCR may also be used to produce variations on the 15 kDa selenoprotein cDNA sequences disclosed herein. Such variants may be variants that are optimized for codon preference in a host cell that is to be used to express the protein, or other sequence changes that facilitate expression. By way of example, it is known that mammalian selenium-containing proteins are very difficult to express in bacteria, yeast or insect cells. Accordingly, in order to facilitate expression of the protein in these cells, a sequence variant may be produced in which the TGA codon (encoding selenocysteine) is replaced with a codon encoding cysteine (either TCT or TGT). However, as described above, it is possible to generate the 15 kDa human selenoprotein without such a mutation.

Two types of cDNA sequence variant may be produced. In the first type, the variation in the cDNA sequence is not manifested as a change in the amino acid sequence of the encoded polypeptide. These "silent" variations are simply a reflection of the degeneracy of the genetic code. In the second type, the cDNA sequence variation does result in a change in the amino acid sequence of the encoded protein, such as the U to C variation discussed above. In such cases, the variant cDNA sequence produces a variant polypeptide sequence. In order to preserve the functional and immunologic identity of the encoded polypeptide, it is preferred that any such amino acid substitutions are "conservative." Conservative substitutions replace one amino acid with another amino acid that is similar in size, hydrophobicity, etc. Examples of conservative substitutions are shown in Table 4 below.

TABLE 4

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an anti-15 kDa selenoprotein antibody; a variant that is recognized by such an antibody is immunologically conserved. Any cDNA sequence variant will preferably introduce no more than 20, and preferably fewer than 10 amino acid substitutions into the encoded polypeptide.

Example 2

Obtaining 15 kDa Selenoprotein Genomic Genes

Having provided herein the cDNA sequence of the human and mouse 15 kDa selenoprotein cDNAs, cloning of the corresponding genomic nucleotide sequences is now enabled. These genomic sequences may readily be obtained by standard laboratory methods, such as RACE-PCR amplification using a human genomic DNA library or genomic DNA extracted directly from human or murine cells as a template.

Having the intron sequence data for the genomic sequence will be valuable for diagnostic applications, e.g., looking for splice-site mutations. The various applications described below (e.g., expression of the 15 kDa selenoprotein for use in producing antibodies) are described using a 15 kDa selenoprotein cDNA sequence, but may also be performed using the corresponding genomic sequence.

Example 3

Expression and Purification of 15 kDa Selenoprotein Polypeptides

With the provision of 15 kDa selenoprotein cDNA sequences, the expression and purification of corresponding 15 kDa selenoprotein polypeptides by standard laboratory techniques is now enabled. The purified polypeptide may be used for functional analyses, antibody production and patient therapy. Furthermore, the DNA sequence of the 15 kDa selenoprotein cDNA and the polymorphic cDNAs disclosed above can be manipulated in studies to understand the expression of the gene and the function of its product. In this way, the underlying biochemical defect which results from mutation or reduced expression of the 15 kDa selenoprotein can be established. The polymorphic versions of the 15 kDa selenoprotein cDNA isolated to date and others which may be isolated based upon information contained herein, may be studied in order to detect alteration in expression patterns in terms of relative quantities, tissue specificity and functional properties of the encoded 15 kDa selenoprotein.

As noted above, for expression in prokaryotic, yeast and insect cells, it is possible to use a sequence variant in which the TGA codon encoding selenocysteine at position 93 is replaced with a codon encoding cysteine (such as TCT or TGT) (for convenience, in the following discussion, this variant form of the protein is still referred to as the 15 kDa selenoprotein). Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to the 15 kDa selenoprotein may be used to prepare polyclonal and monoclonal antibodies against the protein. Thereafter, these antibodies may be used to purify proteins by immunoaffinity chromatography, in diagnostic assays to quantitate the levels of protein, and to localize proteins in tissues and individual cells by immunofluorescence.

The sequence variant or the native protein may also be produced in *E. coli* in large amounts for functional studies. Methods and plasmid vectors for producing fusion proteins and intact native proteins in bacteria are described in Sambrook et al. (In *Molecular Cloning: A Laboratory Manual*, Cold Spring Harbor, N.Y., 1989, chapter 17). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, Cold Spring Harbor, N.Y., 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Cold Spring Harbor, N.Y., 1989, chapter 17).

Vector systems suitable for the expression of lacZ fusion genes include the pUR series of vectors (Ruther and Muller-Hill, 1983, *EMBO J.* 2:1791), pEX1-3 (Stanley and Luzio, 1984, *EMBO J.* 3:1429) and pMR100 (Gray et al., 1982, *Proc. Natl. Acad. Sci. USA* 79:6598). Vectors suitable for the production of intact native proteins include pKC30 (Shimatake and Rosenberg, 1981, *Nature* 292:128), pKK 177-3 (Amann and Brosius, 1985, *Gene* 40:183) and pET-3 (Studiar and Moffatt, 1986, *J. Mol. Biol.* 189:113). 15 kDa selenoprotein fusion proteins may be isolated from protein gels, lyophilized, ground into a powder and used as an antigen. The DNA sequence can also be transferred to other cloning vehicles, such as other plasmids, bacteriophages, cosmids, animal viruses and yeast artificial chromosomes (YACs) (Burke et al., 1987, *Science* 236:806–12). These vectors may then be introduced into a variety of hosts including somatic cells, and simple or complex organisms, such as bacteria, fungi (Timberlake and Marshall, 1989, *Science* 244:1313–7), invertebrates, plants (Gasser and Fraley, 1989, *Science* 244:1293), and mammals (Pursel et al., 1989, *Science* 244:1281–8), which cell or organisms are rendered transgenic by the introduction of the heterologous 15 kDa selenoprotein cDNA.

For expression in mammalian cells, the cDNA sequence need not be modified to remove the selenocysteine codon. Rather, the 15 kDa selenoprotein cDNA may be directly ligated to heterologous promoters, such as the simian virus SV40 promoter in the pSV2 vector (Mulligan and Berg, 1981, *Proc. Natl. Acad. Sci. USA* 78:2072–6), and introduced into cells, such as monkey COS-1 cells (Gluzman, 1981, *Cell* 23:175–82), to achieve transient or long-term expression. The stable integration of the chimeric gene construct may be maintained in mammalian cells by biochemical selection, such as neomycin (Southern and Berg, 1982, *J. Mol. Appl. Genet.* 1:327–41) and mycophoenolic acid (Mulligan and Berg, 1981, *Proc. Natl. Acad. Sci. USA* 78:2072–6). Normal mammalian cell growth medium contains sufficient trace selenium to permit efficient expression of the 15 kDa selenoprotein (for example, selenium is present in fetal bovine serum). However, the growth medium could be enriched if desired by the addition of selenite ($Na_2SeO_3$).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit transcription of the cDNA eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., 1981, *Proc. Natl. Acad. Sci. USA* 78:2072–6; Gorman et al., 1982, *Proc. Natl. Acad. Sci USA* 78:6777–81). The level of expression of the cDNA can be manipulated with this type of vector, either by using promoters that have different activities, for example, the baculovirus pAC373 can express cDNAs at high levels in *Spodptera frugiperda* cells (Summers and Smith, 1985, In: *Genetically Altered Viruses and the Environment*, Fields et al. (Eds.) 22:319–28, Cold Spring Harbor Laboratory Press, Cold Spring Harbor, N.Y.) or by using vectors that contain promoters amenable to modulation, for example, the glucocorticoid-responsive promoter from the mouse mammary tumor virus (Lee et al., 1982, *Nature* 294:228). The expression of the cDNA can be monitored in the recipient cells 24 to 72 hours after introduction (transient expression).

In addition, some vectors contain selectable markers such as the Et (Mulligan and Berg, 1981, *Proc. Natl. Acad. Sci. USA* 78:2072–6) or neo (Southern and Berg, 1982, *J. Mol. Appl. Genet.* 1:327–41) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., 1981, *Mol. Cell Biol.* 1:486) or Epstein-Barr (Sugden et al., 1985, *Mol. Cell Biol.* 5:410). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., 1978, *J. Biol. Chem.* 253:1357).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973, *Virology* 52:466) or strontium phosphate (Brash et al., 1987, *Mol. Cell Biol.* 7:2013), electroporation (Neumann et al., 1982, *EMBO J* 1:841), lipofection (Felgner et al., 1987, *Proc. Natl. Acad. Sci USA* 84:7413), DEAE dextran (McCuthan et al., 1968, *J. Natl Cancer Inst.* 41:351), microinjection (Mueller et al., 1978, *Cell* 15:579), protoplast fusion (Schafner, 1980, *Proc. Natl. Acad. Sci. USA* 77:2163–7), or pellet guns (Klein et al., 1987, *Nature* 327:70). Alternatively, the cDNA can be introduced by infection with virus vectors. Systems are developed that use, for example, retroviruses (Bernstein et al., 1985, *Gen. Engr'g* 7:235), adenoviruses (Ahmad et al., 1986, *J. Virol.* 57:267), or Herpes virus (Spaete et al., 1982, *Cell* 30:295).

These eukaryotic expression systems can be used for studies of the 15 kDa selenoprotein gene and variant forms of this gene, the 15 kDa selenoprotein and variant forms of this protein. Such uses include, for example, the identification of regulatory elements located in the 5' region of the 15 kDa selenoprotein gene on genomic clones that can be isolated from human genomic DNA libraries using the information contained herein. The eukaryotic expression systems may also be used to study the function of the normal complete protein, specific portions of the protein, or of naturally occurring or artificially produced mutant proteins.

Using the above techniques, the expression vectors containing the 15 kDa selenoprotein gene or cDNA sequence or fragments or variants or mutants thereof can be introduced into human cells, mammalian cells from other species or non-mammalian cells as desired. For example, monkey COS cells (Gluzman, 1981, Cell 23:175–82) that produce high levels of the SV40 T antigen and permit the replication of vectors containing the SV40 origin of replication may be used. Similarly, Chinese hamster ovary (CHO), mouse N1H 3T3 fibroblasts or human fibroblasts or lymphoblasts may be used.

Expression of the 15 kDa selenoprotein in eukaryotic cells may be used as a source of proteins to raise antibodies. The 15 kDa selenoprotein may be extracted following release of the protein into the supernatant as described above, or, the cDNA sequence may be incorporated into a eukaryotic expression vector and expressed as a chimeric protein with, for example, β-globin. Antibody to β-globin is thereafter used to purify the chimeric protein. Corresponding protease cleavage sites engineered between the β-globin gene and the cDNA are then used to separate the two polypeptide fragments from one another after translation. One useful expression vector for generating β-globin chimeric proteins is pSG5 (Stratagene). This vector encodes rabbit β-globin.

The present invention thus includes recombinant vectors comprising the selected DNA of the DNA sequences of this invention (e.g., the entire 15 kDa selenoprotein cDNA) for expression in a suitable host. The DNA is operatively linked in the vector to an expression control sequence in the recombinant DNA molecule so that the 15 kDa selenoprotein can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transformed with the vector of this invention, may be selected from the group consisting of bacteria; yeast; fungi; plant; insect; mouse or other animal; or human tissue cells.

It is appreciated that for mutant or variant DNA sequences, similar systems are employed to express and produce the mutant or variant product.

Example 4

Production of Anti-15 kDa Selenoprotein Antibodies a. Production of an Antibody to the 15 kDa Selenoprotein Monoclonal or polyclonal antibodies may be produced to the 15 kDa selenoprotein or portions thereof. Optimally, antibodies raised against the 15 kDa selenoprotein will specifically detect the 15 kDa selenoprotein. That is, antibodies raised against the 15 kDa selenoprotein would recognize and bind the 15 kDa selenoprotein and would not substantially recognize or bind to other proteins found in human cells. The determination that an antibody specifically detects the 15 kDa selenoprotein is made by any one of a number of standard immunoassay methods; for instance, the Western blotting technique (Sambrook et al., In *Molecular Cloning: A Laboratory Manual*, Cold Spring Harbor, N.Y., 1989). To determine that a given antibody preparation (such as one produced in a mouse against the human 15 kDa selenoprotein) specifically detects the 15 kDa selenoprotein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the 15 kDa selenoprotein will, by this technique, be shown to bind substantially only the 15 kDa selenoprotein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-15 kDa selenoprotein binding.

Antibodies that specifically bind to the 15 kDa selenoprotein belong to a class of molecules that are referred to herein as "specific binding agents." Specific binding agents that are capable of specifically binding to the 15 kDa selenoprotein may include polyclonal antibodies, monoclonal antibodies (including humanized monoclonal antibodies) and fragments of monoclonal antibodies such as Fab, F(ab')2 and Fv fragments, as well as any other agent capable of specifically binding to the 15 kDa selenoprotein.

Substantially pure 15 kDa selenoprotein suitable for use as an immunogen is isolated from transfected or transformed cells as described above. Concentration of protein in the final preparation is adjusted, for example, by concentration on an Amicon filter device, to the level of a few micrograms per milliliter Alternatively, peptide fragments of the 15 kDa selenoprotein may be utilized as immunogens. Such fragments may be chemically synthesized using standard methods, or may be obtained by cleavage of the whole 15kDa selenoprotein followed by purification of the desired peptide fragments. Peptides as short as 3 or 4 amino acids in length are immunogenic when presented to the immune system in the context of a Major Histocompatibility Complex (MHC) molecule, such as MHC class I or MHC class II. Accordingly, peptides comprising at least 3 and preferably at least 4, 5, 6 or more consecutive amino acids of the disclosed 15 kDa selenoprotein amino acid sequences may be employed as immuogens to raise antibodies. Because naturally occurring epitopes on proteins are frequently comprised of amino acid residues that are not adjacently arranged in the peptide when the peptide sequence is viewed as a linear molecule, it may be advantageous to utilize longer peptide fragments from the 15 kDa selenoprotein amino acid sequences in order to raise antibodies. Thus, for example, peptides that comprise at least 10, 15, 20, 25 or 30 consecutive amino acid residues of the 15 kDa selenoprotein amino acid sequence may be employed. Monoclonal or polyclonal antibodies to the intact 15 kDa selenoprotein or peptide fragments of this protein may be prepared as described below.

b. Monoclonal Antibody Production by Hybridoma Fusion

Monoclonal antibody to epitopes of the 15 kDa selenoprotein identified and isolated as described can be prepared from murine hybridomas according to the classical method of Kohler and Milstein (*Nature* 256:495, 1975) or derivative methods thereof Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, Cold Spring Harbor Laboratory, New York, 1988). In addition, protocols for producing humanized forms of monoclonal antibodies (for therapeutic applications) and fragments of monoclonal antibodies are known in the art.

c. Polyclonal Antibody Production by Immunization

Polyclonal antiserum containing antibodies to heterogenous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol Metab.* 33:988–91, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. In: *Handbook of Experimental Immunology*, Wier, D. (ed.) chapter 19, Blackwell, 1973. Plateau concentration of antibody is usually in the range of 0.1 to 0.2 mg/ml of serum (about 12 $\mu$M). Affinity of the antisera for the antigen is determined by preparing competitive binding curves, as described, for example, by Fisher (1980).

d. Antibodies Raised by Injection of 15 kDa Selenoprotein cDNA

Antibodies may be raised against the 15 kDa selenoprotein by subcutaneous injection of a DNA vector which expresses the 15 kDa selenoprotein into laboratory animals, such as mice. Delivery of the recombinant vector into the animals may be achieved using a hand-held form of the Biolistic system (Sanford et al., 1987, *Particulate Sci. Technol.* 5:27–37) as described by Tang et al. (*Nature* 356:152–4, 1992). Expression vectors suitable for this purpose may include those which express the 15 kDa selenoprotein cDNA under the transcriptional control of either the human β-actin promoter or the cytomegalovirus (CMV) promoter. Methods of administering naked DNA to animals in a manner to cause expression of that DNA in the body of the animal are well known and are described, for example, in U.S. Pat. No. 5,620,896 ("DNA vaccines against rotavirus infections"), U.S. Pat. No. 5,643,578 ("Immunization by inoculation of DNA transcription unit") and U.S. PAT. NO. 5,593,972 ("Genetic immunization"), and references cited therein.

e. Antibody Fragments

Antibody fragments may be used in place of whole antibodies and may be readily expressed in prokaryotic host cells. Methods of making and using immunologically effective portions of monoclonal antibodies, also referred to as antibody fragments, are well known and include those described in Better and Horowitz (*Methods Enzymol.* 178:476–496, 1989), Better et al. (Advances in Gene Technology: The Molecular Biology of Immune Disease & the Immune Response (ICSU SHort Reports), Streilein et al., eds. vol. 10:105, 1990), Glockshuber et al. (*Biochemistry* 29: 1362–7, 1990), and U.S. Pat. No. 5,648,237 ("Expression of Functional Antibody Fragments"), U.S. Pat. No. 4,946,778 ("Single Polypeptide Chain Binding Molecules"), and U.S. Pat. No. 5,455,030 ("Immunotherapy Using Single Chain Polypeptide Binding Molecules"), and references cited therein.

f. Humanized Antibodies

Humanized monoclonal antibodies are preferred in clinical applications. Methods of making humanized monoclonal antibodies are well known, and include those described in U.S. Pat. No. 5,585,089 ("Humanized Immunoglobulins"), U.S. Pat. No. 5,565,332 ("Production of Chimeric Antibodies—A Combinatorial Approach"), U.S. Pat. No. 5,225,539 ("Recombinant Altered Antibodies And Methods Of Making Altered Antibodies"), U.S. Pat. No. 5,693,761 ("Polynucleotides Encoding Improved Humanized Immunoglobulins"), U.S. Pat. No. 5,693,762 ("Humanized Immunoglobulins"), U.S. Pat. No. 5,585,089 ("Humanized Immunoglobulins"), and U.S. Pat. No. 5,530,101 ("Humanized Immunoglobulins"), and references cited therein.

Antibody preparations prepared according to these protocols are useful in quantitative immunoassays to determine concentrations of antigen-bearing substances in biological samples; they are also used semi-quantitatively or qualitatively to identify the presence of antigen in a biological sample.

Example 5

Detection of Mutations Variants and Polymorphisms

One application of the 15 kDa selenoprotein cDNA sequence information presented herein is in the area of genetic testing, carrier detection and prenatal diagnosis for mutations in the 15 kDa selenoprotein gene sequence. Individuals carrying mutations in the 15 kDa selenoprotein gene (disease carrier or patients) may be detected at the DNA or RNA level with the use of a variety of techniques. For such a diagnostic procedure, a biological sample of the subject, containing either DNA or RNA derived from the subject, is assayed for the presence of a mutant 15 kDa selenoprotein gene. Suitable biological samples include samples containing genomic DNA or RNA obtained from body cells, such as those present in peripheral blood, urine, saliva, tissue biopsy, surgical specimen, amniocentesis samples and autopsy material. Alternatively, the assay may be performed on cDNA made from mRNA obtained from a biological sample. The detection of mutations in the 15 kDa selenoprotein gene may be detected using single-strand conformational polymorphism (SSCP) analysis. The detection in the biological sample of either a mutant 15 kDa selenoprotein gene or a mutant 15 kDa selenoprotein RNA may also be performed by a number of other methodologies known in the art, as outlined below. In particular, the presence of the polymorphic form C811/G1125 may be detected by such means.

Generically, methods for detecting polymorphisms in a gene sequence may be performed using probes that specifically hybridize to either only the wild-type gene sequence or only a particular polymorphic form of that sequence. Thus, a method for detecting a polymorphism in a human 15 kDa selenoprotein gene, cDNA or RNA in a biological sample, comprises hybridizing the sample with a nucleic acid probe under conditions whereby the probe will hybridize to 15 kDa selenoprotein gene, cDNA or RNA carrying a specified particular polymorphism, such as T811, A1125 or T811/A1125, but not to the other polymorphism of the 15 kDa selenoprotein gene, cDNA or RNA (C811]/G1125). For such purposes, the human "wild-type" sequence is considered to be that shown in Seq. I.D. No. 2.

Another suitable detection technique is the polymerase chain reaction amplification of reverse transcribed RNA (RT-PCR) of RNA isolated from lymphocytes followed by direct DNA sequence determination of the products. The presence of one or more nucleotide differences between the obtained sequence and the 15 kDa selenoprotein cDNA sequence presented herein, and especially, differences in the ORF or SECIS portions of the nucleotide sequence are taken as indicative of a potential 15 kDa selenoprotein gene mutation.

Because of the diploid nature of the human genome, both copies of the 15 kDa selenoprotein gene need to be examined to distinguish between heterozygotes and homozygotes. A person who is heterozygous for a mutant form of the 15 kDa selenoprotein (i.e., having one mutant form and one "normal" form) may nevertheless be unaffected by the presence of the mutation. Primer extension, or restriction digestion analysis allows for the rapid determination of the genotype of an individual, as described above.

Alternatively, DNA extracted from lymphocytes or other cells may be used directly for amplification. The direct amplification from genomic DNA would be appropriate for analysis of the entire 15 kDa selenoprotein gene including regulatory sequences located upstream and downstream from the open reading frame. Reviews of direct DNA diagnosis have been presented by Caskey (*Science* 236:1223–8, 1989) and by Landegren et al. (*Science* 242:229–37, 1989).

Further studies of 15 kDa selenoprotein genes isolated from cancer patients may reveal particular mutations/polymorphisms that occur at a high frequency within this population of individuals. In this case, rather than sequencing the entire 15 kDa selenoprotein gene, it may be possible to design DNA diagnostic methods to specifically detect the most common mutations.

The detection of specific DNA mutations may be achieved by methods such as hybridization using specific oligonucleotides (Wallace et al., 1986, *Cold Spring Harbor Symp. Quant. Biol.* 51:257–61), direct DNA sequencing (Church and Gilbert, 1988, *Proc. Natl. Acad. Sci. USA* 81:1991–5), the use of restriction enzymes (Flavell et al., 1978, *Cell* 15:25; Geever et al., 1981, *Proc. Natl. Acad. Sci USA* 78:5081), discrimination on the basis of electrophoretic mobility in gels with denaturing reagent (Myers and Maniatis, 1986, *Cold Spring Harbor Symp. Quant. Biol.* 51:275–84), RNase protection (Myers et al., 1985, *Science* 230:1242), chemical cleavage (Cotton et al., 1985, *Proc.* *Natl. Acad. Sci. USA* 85:4397–4401), and the ligase-mediated detection procedure (Landegren et al., 1988, *Science* 241:1077).

By way of example, oligonucleotides specific to normal or mutant sequences may be chemically synthesized using commercially available machines, labelled radioactively with isotopes (such as alp) or non-radioactively with tags such as biotin (Ward and Langer, 1981, *Proc. Natl. Acad Sci USA* 78:6633–57), and hybridized to individual DNA samples immobilized on membranes or other solid supports by dot-blot or transfer from gels after electrophoresis. The presence or absence of these specific sequences may then be visualized by methods such as autoradiography or fluorometric (Landegren, et al., 1989, *Science* 242:229–37) or colorimetric reactions (Gebeyehu et al., 1987, *Nucl. Acids Res.* 15:4513–34).

Sequence differences between normal and mutant forms of that gene may also be revealed by the direct DNA sequencing method of Church and Gilbert (*Proc. Natl. Acad. Sci. USA* 81:1991–5, 1988). Cloned DNA segments may be used as probes to detect specific DNA segments. The sensitivity of this method is greatly enhanced when combined with PCR (Wrichnik et al., 1987, *Nucleic Acids Res.* 15:52942; Wong et al., 1987 *Nature* 330:384–6; Stoflet et al., 1988, *Science* 239:4914). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, 1975, *J. Mol. Biol.* 98:503). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (Nagamine et al., 1989, *Am. J. Hum. Genet.* 45:337–9). DNA fragments of different sequence compositions may be distinguished on denaturing formamide gradient gels in which the mobilities of different DNA fragments are retarded in the gel at different positions according to their specific "partial-melting" temperatures (Myers et al., 1985, *Science* 230:1242). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., 1989, *Proc. Nat. Acad. Sci. USA* 86:6230–4). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If more than one mutation is frequently encountered in the 15 kDa selenoprotein gene, a system capable of detecting such multiple mutations would be desirable. For example, a PCR with multiple, specific oligonucleotide primers and hybridization probes may be used to identify all possible mutations at the same time (Chamberlain et al., 1988, *Nucl. Acids Res.* 16:1141–55). The procedure may involve immobilized sequence-specific oligonucleotides probes (Saiki et al., 1989, *Proc. Nat. Acad. Sci. USA* 86:6230–4).

One method that is expected to be particularly suitable for detecting mutations in the 15 kDa selenoprotein gene is the use of high density oligonucleotide arrays (also known as "DNA chips") as described by Hacia et al. (*Nature Genetics* 14:441–7, 1996).

Example 6

Detection and Quantification or 15 kDa Sclenoprotein mRNA and Polypeptide

The compositions of the present invention, including 15 kDa selenoprotein-specific antibodies and nucleic acid probes and primers, may be used to detect and/or quantify the level of 15 kDa selenoprotein polypeptide or mRNA in a biological sample. Biological samples suitable for analysis include biopsy samples, such as tumor biopsies, and biological fluids containing cellular material, such as blood, cerebrospinal fluid and saliva.

Determining and/or quantifying the levels of 15 kD selenoprotein polypeptide and mRNA would be useful for detecting reduced levels of the 15 kDa selenoprotein and mRNA which result from, for example, mutations in the promoter regions of the 15 kDa selenoprotein gene or mutations within the coding region of the gene which produce truncated, non-functional polypeptides. In addition, such determinations may provide valuable information about the ability of the cell to incorporate selenium into proteins, as well as information about oxidative stress. Abnormally low levels of 15 kDa selenoprotein polypeptide or mRNA may be indicative of the presence of cancer; such measurements may also be useful to measure the efficacy of cancer treatment.

The determination of reduced 15 kDa selenoprotein polypeptide or mRNA levels would be an alternative or supplemental approach to the direct determination of a patient's status by nucleotide sequence determination outlined above. The availability of antibodies specific to the 15 kDa selenoprotein polypeptide allows the quantitation of cellular 15 kDa selenoprotein polypeptide by one of a number of immunoassay methods which are well known in the art and are presented in Harlow and Lane (*Antibodies, A Laboratory Manual*, Cold Spring Harbor Laboratory, New York, 1988). Such methods include antibody capture assays, antigen capture assays and two antigen sandwich assays. For certain assays, a detectable label may be conjugated to the antibody. Suitable detectable labels include radioactive labels, fluorescent labels and enzymes. Detection and quantification of 15 kDa selenoprotein mRNA levels in a biological sample may be achieved using the probes and primers described above in conjunction with standard laboratory techniques, including quantitative RT-PCR and Northern blotting.

A significant (preferably 50% or greater) reduction in the amount of 15 kDa selenoprotein polypeptide in the cells of a subject compared to the amount of 15 kDa selenoprotein polypeptide found in control ("healthy") cells would be taken as an indication that the subject may be suffering from, or at risk from, cancer.

The present invention also encompasses kits suitable for the detection and quantification of 15 kDa selenoprotein polypeptide or mRNA in biological specimens. Kits suitable for detecting and/or quantifying the polypeptide comprise a container holding a 15 kDa selenoprotein polypeptide-specific binding agent, such as a monoclonal antibody. In certain embodiments, the antibody may be bound to a solid substrate, such as a column or microtiter plate well. In other embodiments, the kit may further include a second specific binding agent that specifically binds to either the 15 kDa selenoprotein polypeptide, or the first specific binding agent. The second specific binding agent may be conjugated with a label molecule that facilitates detection of the second agent when bound to its target. Suitable label molecules are well known in the art and include enzymes, fluorophores and radionuclides. Kits suitable for detecting or quantifying the 15 kDa selenoprotein mRNA comprise a container holding one of more nucleic acid primers or probes as provided above. In certain embodiments, the nucleic acid probes may be conjugated to a suitable label molecule that facilitates detection of the probe when bound to its target. Suitable label molecules are known in the art and include radionuclides and biotin.

An alternative approach to detecting and quantifying levels of the 15 kDa selenoprotein in cells or in an animal is to use the $^{75}$Se isotope. This may be accomplished by a number of methods, including incubating cells with this isotope or administering the isotope to an animal in the diet, following by measurement of the amount of 15 kDa selenoprotein by methods that permit quantification of the level of incorporated radioisotope.

Example 7

Assay of Candidate Agents

The invention also provides methods for screening compounds for their ability to inhibit, facilitate or modulate the expression of 15 kDa selenoprotein polypeptide and mRNA molecules, for use in the in vitro screening of novel agonist and antagonist compounds. Such compounds include candidate cancer therapeutics, such as candidate prostate cancer therapeutics. In general practice such methods comprise measuring 15 kDa selenoprotein polypeptide or mRNA levels in mammalian cells, treating those cells with the candidate agent, and then measuring the 15 kDa selenoprotein polypeptide or mRNA levels to determine what effect, if any, the agent had on expression.

In certain embodiments, the cells to which the candidate agent is administered may be cultured in vitro. Suitable cell lines include human tumor and non-rumor cell lines available from public collections, such as ATCC (Manassas, Va.). Alternatively, the testing of such candidate agents may be performed in laboratory animals, such as mice or rats. Measurement of the levels of 15 kDa selenoprotein polypeptide or mRNA in this latter situation may be accomplished by analysis of biopsy samples or cells from bodily fluids, such as blood. The levels of 15 kDa selenoprotein polypeptide and/or mRNA may be performed using reagents and methods described above.

Example 8

Animal Models

The development of non-human animal models in which a particular gene function has been eliminated has proven invaluable in the development and assessment of new therapeutic agents for diseases such as cancer. With the availability of the mouse 15 kDa selenoprotein polypeptide cDNA and gene sequences, standard technologies may be utilized to produce a mouse or other animal model in which the function of the 15 kDa selenoprotein polypeptide is eliminated (functionally deleted) or reduced. Such gene knockout models may be generated using the methods known in the art, including those described in U.S. Pat. No. 5,616,491 ("Knockout mice"), U.S. Pat. No. 5,714,667 ("Mice lacking expression of CTLA-4 receptor"), U.S. Pat. No. 5,569,824 ("Transgenic mice containing a disrupted p53 gene"), and U.S. Pat. No. 5,557,032 ("Knockout mice") and references cited therein.

In addition, transgenic non-human animal models overexpressing the 15 kDa selenoprotein polypeptide, or variant or mutated versions of the polypeptide are useful for the assessment of agents, such as agonists and antagonists of the polypeptide. Thus, the mouse 15 kDa selenoprotein polypeptide cDNA may be employed in conjunction with known methodologies for creating transgenic mice that over-express an introduced nucleic acid sequence to produce useful animal models. Suitable techniques for generating such transgenic animal models include those described in U.S. Pat. No. 5,489,742 ("Transgenic rats and animal models of inflammatory disease"), U.S. Pat. No. 5,489,743 ("Transgenic animal models for thrombocytopenia"), U.S. Pat. No. 5,304,489 ("DNA sequences to target proteins to the mammary gland for efficient secretion"), U.S. Pat. No. 5,476,995 ("Peptide production"), and U.S. Pat. No. 5,487,992 ("Cells and non-human organisms containing predetermined genomic modifications and positive-negative selection methods and vectors for making same"), and references cited therein.

The relationship between the 15 kDa selenoprotein may be further explored by the creation of double transgenic mice, transgenic for oncogene sequences as well as nucleic acids that encode the 15 kDa selenoprotein. In addition, nucleic acids encoding the 15 kDa selenoprotein may be introduced into tumor cells, which cells may then be used to study tumorigenesis in laboratory animal models, such as mice.

In addition, conditional gene silencing (targeting) can be used to generate transgenic mice (for reviews see Porter, 1998, *Trends Genetics*, vol. 14; Rajewsky et al., 1996, *J. Clin. Invest.* 98:S51–S53). Conditional silencing of a gene allows cells to accumulate prior to the inactivation (functional deletion) of the gene. This approach is advantageous for several reasons. If the gene of interest is an essential gene, mutations in that gene might be lethal, leaving no mouse to study gene function. In addition, this method allows one to generate models of somatically acquired genetic diseases, such as most forms of cancer, rather than of inherited ones. The strategy of this method utilizes the bacteriophage-derived Cre-lox system. The Cre enzyme recognizes a sequence motif of 34 bp, called loxP. If a DNA segment is flanked by two loxP sites in the same orientation, Cre excies that segment from the DNA, leaving a single loxP site behind. Conditional targeting is accomplished by crossing responder mice, carrying the loxP flanked target gene, with regulator mice carrying the Cre transgene, which is expressed in a cell-type-specific or inducible manner.

Example 9

Dietary selenium

As described above, the present invention describes for the first time the existence of the 15 kDa selenoprotein, provides evidence of a link between low levels of this protein and cancer, and provides methods for determining levels of the 15 kDa selenoprotein. Supplementation of the diet with selenium represents one way in which the level of the 15 kDa selenoprotein may be enhanced, with the goal of reducing susceptibility to cancer in patients with a predetermined genetic susceptibility.

Thus, the present invention provides a method for enhancing the level of the 15 kDa selenoprotein in a mammal, by administering to the mammal a dietary selenium supplement. In one embodiment, the method involves a prior determination that the level of 15 kDa selenoprotein in the mammal is lower than the measured average for such mammals. Thus, the invention provides a method for dietary regulation in which the level of 15 kDa selenoprotein in the cells of a mammal is measured. If the level is below normal, enhancing the endogenous selenium level is enhanced by providing selenium supplementation in the diet of the mammal. Such supplementation can take the form of an oral supplement, such as the oral administration of 200 µg of selenuium per day, as described by Clark et al. (*JAMA*, 276:1957–63, 1996)

Example 10

Gene Therapy

In some embodiments, the present invention relates to a method of treating tumors by overexpressing the 15 kDa selenoprotein in cells which have an abnormally low amount of the 15 kDa selenoprotein, or in the cells of a patient having a higher risk for cancers associated with low-levels of 15 kDa selenoprotein. These methods may be accomplished by introducing a gene coding for the 15 kDa selenoprotein (or a variant thereof) into the person. A general strategy for transferring genes into donor cells is disclosed in U.S. Pat. No. 5,529,774. Generally, a gene encoding a protein having therapeutically desired effects is cloned into a viral expression vector, and that vector is then introduced into the target organism. The virus infects the cells, and produces the protein sequence in vivo, where it has its desired therapeutic effect. See, for example, Zabner et al. (*Cell* 75:207–16, 1993).

In some of the foregoing examples, it may only be necessary to introduce the genetic or protein elements into certain cells or tissues. For example, in the case of benign nevi and psoriasis, introducing them into only the skin may be sufficient. However, in some instances (i.e. tumors and polycythemia inflammatory fibrosis), it may be more therapeutically effective and simple to treat all of the patient's cells, or more broadly disseminate the vector, for example by intravascular administration.

The nucleic acid sequence encoding at least one therapeutic agent is under the control of a suitable promoter.

Suitable promoters which may be employed include, but are not limited to, the gene's native promoter, retroviral LTR promoter, or adenoviral promoters, such as the adenoviral major late promoter; the cytomegalovirus (CMV) promoter; the Rous Sarcoma Virus (RSV) promoter; inducible promoters, such as the MMTV promoter; the metallothionein promoter; heat shock promoters; the albumin promoter; the histone promoter; the 0-actin promoter, TK promoters; B19 parvovirus promoters; and the ApoAI promoter. However the scope of the present invention is not limited to specific foreign genes or promoters.

The recombinant nucleic acid can be administered to the animal host by any method which allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vaccinia virus, replication-deficient adenovirus strains or poliovirus, or as a non-infectious form such as naked DNA or liposome encapsulated DNA.

Example 11

Viral Vectors for Gene Therapy

Adenoviral vectors may include essentially the complete adenoviral genome (Shenk et al., Curr. Top. Microbial. Immunol. 111:1–39, 1984). Alternatively, the adenoviral vector may be a modified adenoviral vector in which at least a portion of the adenoviral genome has been deleted. In one embodiment, the vector includes an adenoviral 5' ITR (inverted terminal repeats); an adenoviral 3' ITR; an adenoviral encapsidation signal; a DNA sequence encoding a therapeutic agent; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter. In another embodiment, the vector may be an adeno-associated virus (AAV) such as described in U.S. Pat. No. 4,797,368 (Carter et al.) and AAV type 4 (Chiorini et al. J. Virol. 71:6823–33, 1997) and AAV type 5 (Chiorini et al. J. Virol. 73:309–19, 1999)

Such a vector may be constructed according to standard techniques, using a shuttle plasmid which contains, beginning at the 5' end, an adenoviral 5' ITR, an adenoviral encapsidation signal, and an E1 a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid may also include a selectable marker and an origin of replication. The origin of replication may be a bacterial origin of replication. A desired DNA sequence encoding a therapeutic agent may be inserted into the multiple cloning site of the plasmid.

The plasmid may be used to produce an adenoviral vector by homologous recombination with a modified or mutated adenovirus in which at least the majority of the E1 and E3 adenoviral DNA sequences have been deleted. Homologous recombination may be effected through co-transfection of the plasmid vector and the modified adenovirus into a helper cell line, such as 293 cells, by $CaPO_4$ precipitation. The homologous recombination produces a recombinant adenoviral vector which includes DNA sequences derived from the shuttle plasmid between the Not 1 site and the homologous recombination fragment, and DNA derived from the E1 and E3 deleted adenovirus between the homologous recombination fragment and the 3' ITR.

In one embodiment, the adenovirus may be constructed by using a yeast artificial chromosome (or YAC) containing an adenoviral genome according to the method described in Ketner et al. (Proc. Natl. Acad. Sci., USA, 91:6186–90, 1994), in conjunction with the teachings contained herein. In this embodiment, the adenovirus yeast artificial chromosome is produced by homologous recombination in vivo between adenoviral DNA and yeast artificial chromosome plasmid vectors carrying segments of the adenoviral left and right genomic termini. A DNA sequence encoding a therapeutic agent then may be cloned into the adenoviral DNA. The modified adenoviral genome then is excised from the adenovirus yeast artificial chromosome in order to be used to generate adenoviral vector particles as hereinabove described.

The adenoviral particles are administered in an amount effective to produce a therapeutic effect in a host. The exact dosage of adenoviral particles to be administered is dependent upon a variety of factors, including the age, weight, and sex of the patient to be treated, and the nature and extent of the disease or disorder to be treated. The adenoviral particles may be administered as part of a preparation having a titer of adenoviral particles of at least $1\times10^{10}$ pfu/ml, and in general not exceeding $2\times10^{11}$ pfu/ml. The adenoviral particles may be administered in combination with a pharmaceutically acceptable carrier in a volume up to 10 ml. The pharmaceutically acceptable carrier may be, for example, a liquid carrier such as a saline solution, protamine sulfate (Elkins-Sinn, Inc., Cherry Hill, N.J.), or Polybrene (Sigma Chemical).

In another embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus. The vector is generally a replication defective retrovirus particle.

Retroviral vectors are useful as agents to effect retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

New genes may be incorporated into proviral backbones in several general ways. In the most straightforward constructions, the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. Alternatively, two genes may be expressed from a single promoter by the use of an Internal Ribosome Entry Site.

Having illustrated and described the principles of isolating the human 15 kDa selenoprotein cDNA and corresponding gene and its murine homolog, the proteins encoded by these genes and modes of use of these biological molecules, it should be apparent to one skilled in the art that the invention can be modified in arrangement and detail without departing from such principles. We claim all modifications coming within the spirit and scope of the claims presented herein.

We claim:

1. A method of determining if a subject has a prostate cancer, ovarian cancer, fallopian tube cancer, or a lymphoma, comprising determining if a cell of the subject has a reduced expression of a mammalian 15 kDa selenoprotein comprising SEQ ID NO: 4 when compared to expression of the 15 kDa selenoprotein in a control cell, wherein the reduced expression indicates that the subject has cancer, and wherein the cell of the subject is a prostate cell, ovarian cell, fallopian tube cell, or lymphoid cell.

2. The method of claim 1, wherein determining the reduced expression of the mammalian 15 kDa selenoprotein comprises determining whether the expression of the mammalian 15 kDa selenoprotein is reduced by 3–5 fold in the cell of the subject when compared to expression of the 15 kDa selenoprotein in a control cell.

3. The method of claim 1, wherein determining the reduced expression of the mammalian 15 kDa selenoprotein comprises determining whether the expression of the mammalian 15 kDa selenoprotein is reduced by at least 50% in the cell of the subject when compared to expression of the 15 kDa selenoprotein a control cell.

4. The method of claim 1, wherein determining expression of the mammalian 15 kD selenoprotein comprises Western blotting of the mammalian 15 kDa selenoprotein, or Northern blotting of an mRNA coding for the mammalian 15 kDa selenoprotein.

5. The method of claim 1, wherein the cell of the subject is a lymphoid cell.

6. The method of claim 1, wherein determining expression of the mammalian 15 kDa selenoprotein comprises contacting a sample comprising the cell of the subject with a specific binding agent that specially binds to the mammalian 15 kDa selenoprotein under conditions whereby the specific binding agent forms a complex with the 15 kDa selenoprotein present in the sample, and quantifying the complexes.

7. The method of claim 6, wherein the sample is a biological fluid or a biopsy sample.

8. The method of claim 7, wherein the biological fluid is blood.

9. The method of claim 6, wherein the specific binding agent that specifically binds to the mammalian 15 kDa selenoprotein is an antibody.

10. The method of claim 9, wherein the antibody is a polyclonal antibody.

11. The method of claim 9, wherein the antibody is a monoclonal antibody.

12. The method of claim 11, wherein the monoclonal antibody is a humanized monoclonal antibody.

13. The method of claim 9, wherein the antibody is bound to a solid substrate.

* * * * *

UNITED STATES PATENT AND TRADEMARK OFFICE
CERTIFICATE OF CORRECTION

PATENT NO. : 6,849,417 B1
DATED : February 1, 2005
INVENTOR(S) : Gladyshev et al.

It is certified that error appears in the above-identified patent and that said Letters Patent is hereby corrected as shown below:

Title page,
Item [75], Inventors, the fourth-listed inventor "Alan Diamond", should be deleted.

Column 1,
Line 60, "synthetasc" should be -- synthetase --.

Column 3,
Line 62, "t 125" should be -- 1125 --.
Line 65, an end parenthesis -- ) -- should be added after "C" and before "for".

Column 11,
Line 32, "$^{75}$ Se-labeled" should be -- $^{75}$Se-labeled --.

Column 12,
Line 52, "OPF" should be -- ORF --.

Column 13,
Line 57, "eDNAs" should be -- cDNAs --.
Lines 65-66, "obtained from http:J/blast/wustl.edu/blast/executables" should be deleted.

Column 15,
Line 39, "Helix 1" should be -- Helix I --.

Column 17,
Line 31, the end parenthesis ")" should be deleted.

Column 18,
Lines 12, 22 and 52, "DraI" should be -- DraI --.

Column 19,
Line 9, -- and -- should be inserted before "has" and after "selenoprotein)".

Column 20,
Line 2, "–8" should be -- ~8 --.

Column 26,
Line 39, a period -- . -- should be added after "milliliter".

Column 27,
Line 2, a period -- . -- should be added after "thereof".

UNITED STATES PATENT AND TRADEMARK OFFICE
CERTIFICATE OF CORRECTION

PATENT NO. : 6,849,417 B1
DATED : February 1, 2005
INVENTOR(S) : Gladyshev et al.

It is certified that error appears in the above-identified patent and that said Letters Patent is hereby corrected as shown below:

Column 28,
Line 14, "SHort" should be -- Short --.

Column 29,
Line 17, "(C811]/G1125)" should be -- (C811/G1125) --.

Column 30,
Line 25, "4914" should be -- 491-4 --.

Column 35,
Line 8, "0-actin" should be -- $\beta$-actin --.
Line 45, "309-19" should be -- 1309-19 --.

Signed and Sealed this

Eighteenth Day of April, 2006

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 162
<212> TYPE: PRT
<213> ORGANISM: Homo sapiens
<220> FEATURE:
<221> NAME/KEY: SITE
<222> LOCATION: (93)..(93)
<223> OTHER INFORMATION: Xaa is selenocysteine

<400> SEQUENCE: 1

Met Ala Ala Gly Pro Ser Gly Cys Leu Val Pro Ala Phe Gly Lys Arg
1               5                   10                  15

Leu Leu Leu Ala Thr Val Leu Gln Ala Val Ser Ala Phe Gly Ala Glu
            20                  25                  30

Phe Ser Ser Glu Ala Cys Arg Glu Leu Gly Phe Ser Ser Asn Leu Leu
        35                  40                  45

Cys Ser Ser Cys Asp Leu Leu Gly Gln Phe Asn Leu Leu Gln Leu Asp
    50                  55                  60

Pro Asp Cys Arg Gly Cys Cys Gln Glu Glu Ala Gln Phe Glu Thr Lys
65                  70                  75                  80

Lys Leu Tyr Ala Gly Ala Ile Leu Glu Val Cys Gly Xaa Lys Leu Gly
                85                  90                  95

Arg Phe Pro Gln Val Gln Ala Phe Val Arg Ser Asp Lys Pro Lys Leu
            100                 105                 110

Phe Arg Gly Leu Gln Ile Lys Tyr Val Arg Gly Ser Asp Pro Val Leu
        115                 120                 125

Lys Leu Leu Asp Asp Asn Gly Asn Ile Ala Glu Glu Leu Ser Ile Leu
    130                 135                 140

Lys Trp Asn Thr Asp Ser Val Glu Glu Phe Leu Ser Glu Lys Leu Glu
145                 150                 155                 160

Arg Ile

<210> SEQ ID NO 2
<211> LENGTH: 1244
<212> TYPE: DNA
<213> ORGANISM: Homo sapiens
<220> FEATURE:
<221> NAME/KEY: CDS
<222> LOCATION: (5)..(493)
<223> OTHER INFORMATION:
<220> FEATURE:
<221> NAME/KEY: misc_feature
<222> LOCATION: (281)..(283)
<223> OTHER INFORMATION: TGA codon codes for selenocysteine

<400> SEQUENCE: 2 agcg atg gcg gct ggg ccg agt ggg tgt ctg gtg ccg gcg ttt ggg cta      49
     Met Ala Ala Gly Pro Ser Gly Cys Leu Val Pro Ala Phe Gly Leu
     1               5                   10                  15 cgg ttg ttg ttg gcg act gtg ctt caa gcg gtg tct gct ttt ggg gca      97
```

-continued

| | | |
|---|---|---|
| Arg Leu Leu Leu Ala Thr Val Leu Gln Ala Val Ser Ala Phe Gly Ala<br>20 25 30 | | |
| gag ttt tca tcg gag gca tgc aga gag tta ggc ttt tct agc aac ttg<br>Glu Phe Ser Ser Glu Ala Cys Arg Glu Leu Gly Phe Ser Ser Asn Leu<br>35 40 45 | 145 | |
| ctt tgc agc tct tgt gat ctt ctc gga cag ttc aac ctg ctt cag ctg<br>Leu Cys Ser Ser Cys Asp Leu Leu Gly Gln Phe Asn Leu Leu Gln Leu<br>50 55 60 | 193 | |
| gat cct gat tgc aga gga tgc tgt cag gag gaa gca caa ttt gaa acc<br>Asp Pro Asp Cys Arg Gly Cys Cys Gln Glu Glu Ala Gln Phe Glu Thr<br>65 70 75 | 241 | |
| aaa aag ctg tat gca gga gct att ctt gaa gtt tgt gga tga aaa ttg<br>Lys Lys Leu Tyr Ala Gly Ala Ile Leu Glu Val Cys Gly Lys Leu<br>80 85 90 | 289 | |
| gga agg ttc cct caa gtc caa gct ttt gtt agg agt gat aaa ccc aaa<br>Gly Arg Phe Pro Gln Val Gln Ala Phe Val Arg Ser Asp Lys Pro Lys<br>95 100 105 110 | 337 | |
| ctg ttc aga gga ctg caa atc aag tat gtc cgt ggt tca gac cct gta<br>Leu Phe Arg Gly Leu Gln Ile Lys Tyr Val Arg Gly Ser Asp Pro Val<br>115 120 125 | 385 | |
| tta aag ctt ttg gac gac aat ggg aac att gct gaa gaa ctg agc att<br>Leu Lys Leu Leu Asp Asp Asn Gly Asn Ile Ala Glu Glu Leu Ser Ile<br>130 135 140 | 433 | |
| ctc aaa tgg aac aca gac agt gta gaa gaa ttc ctg agt gaa aag ttg<br>Leu Lys Trp Asn Thr Asp Ser Val Glu Glu Phe Leu Ser Glu Lys Leu<br>145 150 155 | 481 | |
| gaa cgc ata taa atcttgctta aattttgtcc tatccttttg ttaccttatc<br>Glu Arg Ile<br>160 | 533 | |
| aaatgaaata ttcagcacc tagaaaataa tttagttttg cttgcttcca ttgatcagtc | 593 | |
| ttttacttga ggcattaaat atctaattaa atcgtgaaat ggcagtatag tccatgatat | 653 | |
| ctaaggagtt ggcaagctta acaaaaccca ttttttataa atgtccatcc tcctgcattt | 713 | |
| gttgatacca ctaacaaaat gctttgtaac agacttgcgg ttaattatgc aaatgatagt | 773 | |
| ttgtgataat tggtccagtt ttacgaacaa cagatttcta aattagagag gttaacaaga | 833 | |
| cagatgatta ctatgcctca tgtgctgtgt gctctttgaa aggaatgaca gcagactaca | 893 | |
| aagcaaataa gatatactga gcctcaacag attgcctgct cctcagagtc tctcctattt | 953 | |
| ttgtattacc cagctttctt tttaatacaa atgttattta tagtttacaa tgaatgcact | 1013 | |
| gcataaaaac tttgtagctt cattattgta aaacatattc aagatcctac agtaagagtg | 1073 | |
| aaacattcac aaagatttgc gttaatgaag actacacaga aaacctttct agggatttgt | 1133 | |
| gtggatcaga tacatacttg gcaaattttt gagtttttaca ttcttacaga aaagtccatt | 1193 | |
| taaaagtgat catttgtaag accaaaatat aaataaaaag tttcaaaaat c | 1244 | |

<210> SEQ ID NO 3
<211> LENGTH: 489
<212> TYPE: DNA
<213> ORGANISM: Homo sapiens
<220> FEATURE:
<221> NAME/KEY: CDS
<222> LOCATION: (1)..(489)
<223> OTHER INFORMATION:
<220> FEATURE:
<221> NAME/KEY: misc_feature
<222> LOCATION: (277)..(279)
<223> OTHER INFORMATION: TGA codon codes for selenocysteine

<400> SEQUENCE: 3

```
atg gcg gct ggg ccg agt ggg tgt ctg gtg ccg gcg ttt ggg cta cgg    48
Met Ala Ala Gly Pro Ser Gly Cys Leu Val Pro Ala Phe Gly Leu Arg
1               5                   10                  15 ttg ttg ttg gcg act gtg ctt caa gcg gtg tct gct ttt ggg gca gag    96
Leu Leu Leu Ala Thr Val Leu Gln Ala Val Ser Ala Phe Gly Ala Glu
            20                  25                  30 ttt tca tcg gag gca tgc aga gag tta ggc ttt tct agc aac ttg ctt   144
Phe Ser Ser Glu Ala Cys Arg Glu Leu Gly Phe Ser Ser Asn Leu Leu
        35                  40                  45 tgc agc tct tgt gat ctt ctc gga cag ttc aac ctg ctt cag ctg gat   192
Cys Ser Ser Cys Asp Leu Leu Gly Gln Phe Asn Leu Leu Gln Leu Asp
50                  55                  60 cct gat tgc aga gga tgc tgt cag gag gaa gca caa ttt gaa acc aaa   240
Pro Asp Cys Arg Gly Cys Cys Gln Glu Glu Ala Gln Phe Glu Thr Lys
65                  70                  75                  80 aag ctg tat gca gga gct att ctt gaa gtt tgt gga tga aaa ttg gga   288
Lys Leu Tyr Ala Gly Ala Ile Leu Glu Val Cys Gly     Lys Leu Gly
                85                  90                  95 agg ttc cct caa gtc caa gct ttt gtt agg agt gat aaa ccc aaa ctg   336
Arg Phe Pro Gln Val Gln Ala Phe Val Arg Ser Asp Lys Pro Lys Leu
            100                 105                 110 ttc aga gga ctg caa atc aag tat gtc cgt ggt tca gac cct gta tta   384
Phe Arg Gly Leu Gln Ile Lys Tyr Val Arg Gly Ser Asp Pro Val Leu
        115                 120                 125 aag ctt ttg gac gac aat ggg aac att gct gaa gaa ctg agc att ctc   432
Lys Leu Leu Asp Asp Asn Gly Asn Ile Ala Glu Glu Leu Ser Ile Leu
    130                 135                 140 aaa tgg aac aca gac agt gta gaa gaa ttc ctg agt gaa aag ttg gaa   480
Lys Trp Asn Thr Asp Ser Val Glu Glu Phe Leu Ser Glu Lys Leu Glu
145                 150                 155 cgc ata taa                                                       489
Arg Ile
160

<210> SEQ ID NO 4
<211> LENGTH: 136
<212> TYPE: PRT
<213> ORGANISM: Homo sapiens
<220> FEATURE:
<221> NAME/KEY: SITE
<222> LOCATION: (67)..(67)
<223> OTHER INFORMATION: Xaa is selenocysteine

<400> SEQUENCE: 4

Ser Ala Phe Gly Ala Glu Phe Ser Glu Ala Cys Arg Glu Leu Gly
1               5                   10                  15

Phe Ser Ser Asn Leu Leu Cys Ser Cys Asp Leu Leu Gly Gln Phe
            20                  25                  30

Asn Leu Leu Gln Leu Asp Pro Asp Cys Arg Gly Cys Cys Gln Glu Glu
        35                  40                  45

Ala Gln Phe Glu Thr Lys Lys Leu Tyr Ala Gly Ala Ile Leu Glu Val
    50                  55                  60

Cys Gly Xaa Lys Leu Gly Arg Phe Pro Gln Val Gln Ala Phe Val Arg
65                  70                  75                  80

Ser Asp Lys Pro Lys Leu Phe Arg Gly Leu Gln Ile Lys Tyr Val Arg
                85                  90                  95

Gly Ser Asp Pro Val Leu Lys Leu Leu Asp Asp Asn Gly Asn Ile Ala
            100                 105                 110

Glu Glu Leu Ser Ile Leu Lys Trp Asn Thr Asp Ser Val Glu Glu Phe
        115                 120                 125
```

```
Leu Ser Glu Lys Leu Glu Arg Ile
    130                 135

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
atggcggctg ggccgagtgg g                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
taatatgcgt tccaactttt c                                              21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tctgcttttg gggcagagtt t                                              21

<210> SEQ ID NO 8
<211> LENGTH: 1216
<212> TYPE: DNA
<213> ORGANISM: Mus musculus
<220> FEATURE:
<221> NAME/KEY: CDS
<222> LOCATION: (11)..(490)
<223> OTHER INFORMATION:
<220> FEATURE:
<221> NAME/KEY: misc_feature
<222> LOCATION: (287)..(289)
<223> OTHER INFORMATION: TGA codon codes for selenocysteine

<400> SEQUENCE: 8
gaccgcaggg atg gcg gca ggg cag ggt ggg tgg ctg cgg cca gct ctg      49
            Met Ala Ala Gly Gln Gly Gly Trp Leu Arg Pro Ala Leu
              1               5                  10 ggg ctg cgc ttg ctg ctg gcg act gcg ttt caa gcg gtg tct gct ctg     97
Gly Leu Arg Leu Leu Leu Ala Thr Ala Phe Gln Ala Val Ser Ala Leu
 15                  20                  25 ggg gca gag ttt gcg tca gag gca tgc aga gag ttg ggt ttc tcc agc     145
Gly Ala Glu Phe Ala Ser Glu Ala Cys Arg Glu Leu Gly Phe Ser Ser
 30                  35                  40                  45 aac ttg ctc tgc agc tct tgc gat ctt ctt gga cag ttt aat ctg ctc     193
Asn Leu Leu Cys Ser Ser Cys Asp Leu Leu Gly Gln Phe Asn Leu Leu
                 50                  55                  60 cca ctg gac cct gtt tgc aga ggg tgc tgt cag gaa gaa gca caa ttt     241
Pro Leu Asp Pro Val Cys Arg Gly Cys Cys Gln Glu Glu Ala Gln Phe
             65                  70                  75 gaa acc aaa aag ctg tat gca gga gcc atc ctt gaa gtc tgc gga tga     289
Glu Thr Lys Lys Leu Tyr Ala Gly Ala Ile Leu Glu Val Cys Gly
         80                  85                  90
```

-continued

```
aaa ttg ggg agg ttc cct caa gtc caa gct ttt gtc aga agt gat aaa       337
Lys Leu Gly Arg Phe Pro Gln Val Gln Ala Phe Val Arg Ser Asp Lys
         95                 100                 105 ccc aaa ctc ttc aga ggt cta cag atc aag tat gtt cga ggc tca gac       385
Pro Lys Leu Phe Arg Gly Leu Gln Ile Lys Tyr Val Arg Gly Ser Asp
    110                 115                 120 cct gta cta aag ctt ttg gac gac aac ggg aac att gct gaa gaa cta       433
Pro Val Leu Lys Leu Leu Asp Asp Asn Gly Asn Ile Ala Glu Glu Leu
125                 130                 135                 140 agc atc ctc aaa tgg aac aca gac agt gtg gaa gag ttc ctg agc gag       481
Ser Ile Leu Lys Trp Asn Thr Asp Ser Val Glu Glu Phe Leu Ser Glu
                145                 150                 155 aag ttg gaa cgcatataaa catgcttagt agtttttata ctaatcaaat               530
Lys Leu Glu gaattatcac agcacctaga caataactta gttttgcatg cttacattgg tcatccttt      590 tatgtacatc attaatcttc tgacaagaag ctgaagtagc accacagtcc ataatatatc     650
aggatctggc aagcttaagg aacccagctc ttagaaattt ctcttcttct acacttgttg     710
ctctcaccag tgaaacgctt tgtaaggagg catctgggta attatgcaaa taagtttgtg     770
ataattgctc cagttctaca acaacagaa ttttaaatag aggaagtgga taaaggagac      830
acctcccttg ctgtgtgctc tttgaaagta attgacagaa aactacaaac acgtaggatg     890
ccctgcgcct cagcagcacc caccccagag cctcttggcg tgcccagctt tcttttcagt    950
acaagtattt gtagtttgta atgaatgtgc cacatacagg ttttgtagct tattattatg    1010
gaacagactg aagatctgca gtacgaatgt aatacttata aaggtttgca ttaatgagga    1070
ttacacagaa aacctttgtt aaggacttgt gtagatctga taattggcaa attttttattt   1130 taaaagtatt cttacagaag agttccattt aagaatgttc acttatagga ccaaaatata    1190
aataaaaact ttcaaatatg aaaaaa                                         1216
```

<210> SEQ ID NO 9
<211> LENGTH: 162
<212> TYPE: PRT
<213> ORGANISM: Mus musculus
<220> FEATURE:
<221> NAME/KEY: SITE
<222> LOCATION: (93)..(93)
<223> OTHER INFORMATION: Xaa is selenocysteine

<400> SEQUENCE: 9

```
Met Ala Ala Gly Gln Gly Gly Trp Leu Arg Pro Ala Leu Gly Leu Arg
1               5                   10                  15

Leu Leu Leu Ala Thr Ala Phe Gln Ala Val Ser Ala Leu Gly Ala Glu
            20                  25                  30

Phe Ala Ser Glu Ala Cys Arg Glu Leu Gly Phe Ser Ser Asn Leu Leu
        35                  40                  45

Cys Ser Ser Cys Asp Leu Leu Gly Gln Phe Asn Leu Leu Pro Leu Asp
    50                  55                  60

Pro Val Cys Arg Gly Cys Cys Gln Glu Glu Ala Gln Phe Glu Thr Lys
65                  70                  75                  80

Lys Leu Tyr Ala Gly Ala Ile Leu Glu Val Cys Gly Xaa Lys Leu Gly
                85                  90                  95

Arg Phe Pro Gln Val Gln Ala Phe Val Arg Ser Asp Lys Pro Lys Leu
            100                 105                 110

Phe Arg Gly Leu Gln Ile Lys Tyr Val Arg Gly Ser Asp Pro Val Leu
        115                 120                 125
```

```
Lys Leu Leu Asp Asp Asn Gly Asn Ile Ala Glu Glu Leu Ser Ile Leu
    130                 135                 140

Lys Trp Asn Thr Asp Ser Val Glu Glu Phe Leu Ser Glu Lys Leu Glu
145                 150                 155                 160

Arg Ile

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
atggcggcag ggcagggtgg                                            20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
tatgcgttcc aacttctcgc t                                          21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cagacttgcg gttaattatg                                            20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gccaagtatg tatctgatcc                                            20

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ggcatagtaa tcatctgtct tgtt                                       24

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
```

-continued gtatgtatct gatccacaca aatcc                                      25

```
<210> SEQ ID NO 16
<211> LENGTH: 152
<212> TYPE: PRT
<213> ORGANISM: Caenorhabditis elegans
<220> FEATURE:
<221> NAME/KEY: SITE
<222> LOCATION: (129)..(129)
<223> OTHER INFORMATION: Xaa is any amino acid

<400> SEQUENCE: 16
```

Gly Trp Val Ile Phe Leu Leu Leu Ala Ala Val Val Ser Pro Met Phe
1               5                   10                  15

Gly Glu Val Glu Glu Tyr Lys Ile Asp Val Glu Glu Cys Lys Ala Ala
            20                  25                  30

Gly Phe Asn Pro Glu Thr Leu Lys Cys Gly Leu Cys Glu Arg Leu Ser
        35                  40                  45

Asp Tyr His Leu Glu Thr Leu Leu Thr Asp Cys Leu Gln Cys Cys Ile
    50                  55                  60

Lys Glu Glu Glu Phe Lys His Glu Lys Tyr Pro Thr Ala Ile Leu Glu
65                  70                  75                  80

Val Cys Glu Cys Asn Leu Ala Arg Phe Pro Gln Val Gln Ala Phe Val
                85                  90                  95

His Lys Asp Met Ala Arg Gln Phe Gly Lys Val Lys Val Lys His
            100                 105                 110

Val Arg Gly Val Arg Pro Gln Val Ala Leu Lys Asp Ala Asp Phe Lys
        115                 120                 125

Xaa Lys Glu Val Leu Ser Val Glu Lys Trp Asp Thr Asp Thr Leu Ile
    130                 135                 140

Asp Phe Phe Asn Gln Trp Leu Glu
145                 150

```
<210> SEQ ID NO 17
<211> LENGTH: 89
<212> TYPE: PRT
<213> ORGANISM: Brugla malayi

<400> SEQUENCE: 17
```

Lys Asp Tyr Ala Glu Met Glu Gln Glu Lys Tyr Pro Arg Ala His Ile
1               5                   10                  15

Glu Ile Cys Glu Cys Asn Leu Gly Arg Phe Pro Gln Ala Glu Ala Phe
            20                  25                  30

Val Lys Ser Asn Met Val Lys Lys Trp Gly Thr Cys Val Lys Val His
        35                  40                  45

His Val Arg Gly Thr Leu Pro Thr Ile Lys Leu Leu Asp Ala Gln Gly
    50                  55                  60

Glu Val Gln Lys Thr Met Asn Ile Glu Lys Trp Asp Thr Asp Thr Ile
65                  70                  75                  80

Thr Glu Phe Leu Asn Thr Trp Leu Glu
                85

```
<210> SEQ ID NO 18
<211> LENGTH: 39
<212> TYPE: PRT
<213> ORGANISM: Oryza sativa

<400> SEQUENCE: 18
```

Gly Arg Arg Leu Val Leu Thr Ser Cys Ser Val Leu Cys Leu Gly Ala

```
                1               5                    10                      15
Glu Gly Phe Gly Ala Arg Glu Cys Glu Glu Leu Gly Phe Thr Gly Leu
                        20                   25                 30

Ala Leu Cys Ser Asp Cys Asn
                35

<210> SEQ ID NO 19
<211> LENGTH: 75
<212> TYPE: DNA
<213> ORGANISM: Homo sapiens

<400> SEQUENCE: 19
gggggttttt  catctatgag  ggtgtttcct  ctaaacctac  gagggaggaa  cacctgatct       60
tacagaaaat  accac                                                           75
```